(12) United States Patent
Thornton

(10) Patent No.: US 8,607,796 B2
(45) Date of Patent: Dec. 17, 2013

(54) APPARATUS AND METHOD FOR COUPLING AN ORAL APPLIANCE TO A GAS DELIVERY DEVICE

(75) Inventor: W. Keith Thornton, Dallas, TX (US)

(73) Assignee: Airway Technologies, LLC, Carrollton, TX (US)

( * ) Notice: Subject to any disclaimer, the term of this patent is extended or adjusted under 35 U.S.C. 154(b) by 806 days.

(21) Appl. No.: 12/712,931

(22) Filed: Feb. 25, 2010

(65) Prior Publication Data

US 2010/0218773 A1    Sep. 2, 2010

Related U.S. Application Data

(60) Provisional application No. 61/156,323, filed on Feb. 27, 2009.

(51) Int. Cl.
*A61F 5/56* (2006.01)
*A62B 18/08* (2006.01)

(52) U.S. Cl.
USPC ..................................... 128/848; 128/206.29

(58) Field of Classification Search
USPC ............ 128/200.24, 201.18, 201.26, 206.29, 128/848, 859, 861, 862
See application file for complete search history.

(56) References Cited

U.S. PATENT DOCUMENTS

| | | |
|---|---|---|
| 339,334 A | 4/1886 | Searle |
| 690,663 A | 1/1902 | Pratt |
| 746,869 A | 12/1903 | Moulton |
| 774,446 A | 11/1904 | Moulton |
| 781,516 A | 1/1905 | Guthrie, Jr. |
| 885,196 A | 4/1908 | Steil |
| 893,213 A | 7/1908 | Whiteway |
| 955,562 A | 4/1910 | Thomas |

(Continued)

FOREIGN PATENT DOCUMENTS

| | | |
|---|---|---|
| DE | 156627 | 12/1904 |
| DE | 2 320 501 | 11/1974 |

(Continued)

OTHER PUBLICATIONS

Craig, William H., et al.; "Skeletal class II treatment with the Chateau appliance," The Journal of Pedondontics (vol. 11:120); pp. 120-138, 1987.

(Continued)

*Primary Examiner* — Nicholas Lucchesi
*Assistant Examiner* — Nathan R Price
(74) *Attorney, Agent, or Firm* — Baker Botts L.L.P.

(57) ABSTRACT

According to one embodiment, an apparatus for coupling an oral appliance to a gas delivery device includes a post, a swivel, and first and second opposing clamps. The post includes a base configured to couple to the oral appliance; a first arm extending from the base and defining a channel extending along a portion of the first arm; and a second arm extending from the base, extending substantially parallel to the first arm, the second arm defining a channel extending along a portion of the second arm. The swivel is substantially spherical and is configured to position the gas delivery device. The first clamp is configured to engage and slide along the channel defined by the first arm and the second clamp is configured to engage and slide along the channel defined by the second arm. The first and second opposing clamps are together configured to position and secure the location and orientation of the swivel relative to the post.

8 Claims, 20 Drawing Sheets

(56) References Cited

U.S. PATENT DOCUMENTS

| | | |
|---|---|---|
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |
| 1,675,202 A | 6/1928 | Warne |
| 1,679,748 A | 8/1928 | Stratton |
| 2,171,695 A | 9/1939 | Harper |
| 2,178,128 A | 10/1939 | Waite |
| 2,383,649 A | 8/1945 | Heidbrink |
| 2,424,533 A | 7/1947 | Faires |
| 2,505,028 A | 4/1950 | Boeger |
| 2,521,039 A | 9/1950 | Carpenter |
| 2,521,084 A | 9/1950 | Oberto |
| 2,531,222 A | 11/1950 | Kesling |
| 2,574,623 A | 11/1951 | Clyde |
| 2,590,118 A | 3/1952 | Oddo, Jr. |
| 2,627,268 A | 2/1953 | Leppich |
| 2,671,446 A | 3/1954 | Mann |
| 2,712,160 A | 7/1955 | Sterczek |
| 2,833,278 A | 5/1958 | Ross |
| 2,867,212 A | 1/1959 | Nunn, Jr. |
| 2,882,893 A | 4/1959 | Godfroy |
| 2,917,045 A | 12/1959 | Schildknecht et al. |
| 2,977,636 A | 4/1961 | McGuire |
| 3,037,501 A | 6/1962 | Miller |
| 3,064,354 A | 11/1962 | Pos |
| 3,107,668 A | 10/1963 | Thompson |
| 3,124,129 A | 3/1964 | Grossberg |
| 3,132,647 A | 5/1964 | Corniello |
| 3,219,033 A | 11/1965 | Wallshein |
| 3,277,892 A | 10/1966 | Tepper |
| 3,312,216 A | 4/1967 | Wallshein |
| 3,321,832 A | 5/1967 | Weisberg |
| 3,330,274 A | 7/1967 | Bennett |
| 3,360,860 A | 1/1968 | Roland |
| 3,434,470 A | 3/1969 | Strickland |
| 3,457,916 A | 7/1969 | Wolicki |
| 3,513,838 A | 5/1970 | Foderick et al. |
| 3,522,805 A | 8/1970 | Wallshein |
| 3,658,058 A | 4/1972 | Neidhart et al. |
| 3,690,004 A | 9/1972 | Frush |
| 3,695,265 A | 10/1972 | Brevik |
| 3,845,768 A | 11/1974 | Garrahan |
| 3,854,208 A | 12/1974 | Arant |
| 3,864,832 A | 2/1975 | Carlson |
| 3,871,370 A | 3/1975 | McDonald |
| 3,882,601 A | 5/1975 | Jahn |
| 3,884,226 A | 5/1975 | Tepper |
| 4,016,650 A | 4/1977 | Leusner et al. |
| 4,026,024 A | 5/1977 | Tradowsky |
| 4,114,614 A | 9/1978 | Kesling |
| 4,169,473 A | 10/1979 | Samelson |
| 4,182,312 A | 1/1980 | Mushabac |
| 4,227,877 A | 10/1980 | Tureaud et al. |
| 4,233,972 A | 11/1980 | Hauff et al. |
| 4,258,710 A | 3/1981 | Reber |
| 4,289,127 A | 9/1981 | Nelson |
| 4,294,243 A | 10/1981 | Ernsting et al. |
| 4,304,227 A | 12/1981 | Samelson |
| 4,345,592 A | 8/1982 | Giorgini et al. |
| 4,345,593 A | 8/1982 | Sullivan |
| 4,376,628 A | 3/1983 | Aardse |
| 4,382,783 A | 5/1983 | Rosenberg |
| 4,392,490 A | 7/1983 | Mattingly et al. |
| 4,397,701 A | 8/1983 | Johnson et al. |
| 4,419,992 A | 12/1983 | Chorbajian |
| 4,433,956 A | 2/1984 | Witzig |
| 4,439,147 A | 3/1984 | Magill et al. |
| 4,439,149 A | 3/1984 | Devincenzo |
| 4,454,090 A | 6/1984 | Saumell |
| 4,470,413 A | 9/1984 | Warncke |
| 4,495,945 A | 1/1985 | Liegner |
| 4,505,672 A | 3/1985 | Kurz |
| 4,530,662 A | 7/1985 | Andersson et al. |
| 4,553,549 A | 11/1985 | Pope et al. |
| 4,568,280 A | 2/1986 | Ahlin |
| 4,569,342 A | 2/1986 | von Nostitz |
| 4,593,686 A | 6/1986 | Lloyd et al. |
| 4,602,905 A | 7/1986 | O'Keefe, III |
| 4,639,220 A | 1/1987 | Nara et al. |
| 4,655,213 A | 4/1987 | Rapoport et al. |
| 4,668,188 A | 5/1987 | Wolfenson et al. |
| 4,669,459 A | 6/1987 | Spiewak et al. |
| 4,676,240 A | 6/1987 | Gardy |
| 4,706,683 A | 11/1987 | Chilton et al. |
| 4,715,368 A | 12/1987 | George |
| 4,741,696 A | 5/1988 | Cetlin |
| 4,773,853 A | 9/1988 | Kussick |
| 4,784,123 A | 11/1988 | Robeson |
| 4,799,500 A | 1/1989 | Newbury |
| 4,858,605 A | 8/1989 | Levy |
| 4,858,606 A | 8/1989 | Hamlin |
| 4,862,903 A | 9/1989 | Campbell |
| 4,870,962 A | 10/1989 | Sitnik |
| 4,886,056 A | 12/1989 | Simpson |
| 4,892,478 A | 1/1990 | Tateosian et al. |
| 4,901,737 A | 2/1990 | Toone |
| 4,906,234 A | 3/1990 | Voychehovski |
| 4,919,128 A | 4/1990 | Kopala et al. |
| 4,932,867 A | 6/1990 | Ueno |
| 4,941,212 A | 7/1990 | Liff |
| 4,955,393 A | 9/1990 | Adell |
| RE33,442 E | 11/1990 | George |
| 5,003,994 A | 4/1991 | Cook |
| 5,011,407 A | 4/1991 | Pelerin |
| 5,018,533 A | 5/1991 | Hawkins |
| 5,026,278 A | 6/1991 | Oxman et al. |
| 5,028,232 A | 7/1991 | Snow |
| 5,040,976 A | 8/1991 | Ubel, III et al. |
| 5,042,478 A | 8/1991 | Kopala et al. |
| 5,042,506 A | 8/1991 | Liberati |
| 5,046,512 A | 9/1991 | Murchie |
| 5,052,409 A | 10/1991 | Tepper |
| 5,055,039 A | 10/1991 | Abbatte et al. |
| 5,056,534 A | 10/1991 | Wright |
| 5,062,421 A | 11/1991 | Burns et al. |
| 5,064,371 A | 11/1991 | Smeltzer |
| 5,065,756 A | 11/1991 | Rapoport |
| 5,066,231 A | 11/1991 | Oxman et al. |
| 5,078,600 A | 1/1992 | Austin |
| 5,092,346 A | 3/1992 | Hays et al. |
| 5,103,838 A | 4/1992 | Yousif |
| 5,112,225 A | 5/1992 | Diesso |
| 5,117,816 A | 6/1992 | Shapiro et al. |
| 5,154,184 A | 10/1992 | Alvarez |
| 5,154,609 A | 10/1992 | George |
| 5,183,057 A | 2/1993 | Syrop et al. |
| 5,188,529 A | 2/1993 | Lüth |
| 5,190,457 A | 3/1993 | Schreinemakers |
| 5,193,532 A | 3/1993 | Moa et al. |
| 5,213,498 A | 5/1993 | Pelerin |
| 5,233,978 A | 8/1993 | Callaway |
| 5,243,971 A | 9/1993 | Sullivan et al. |
| 5,245,995 A | 9/1993 | Sullivan et al. |
| 5,265,595 A | 11/1993 | Rudolph |
| 5,267,557 A | 12/1993 | Her-Mou |
| 5,267,862 A | 12/1993 | Parker |
| 5,277,202 A | 1/1994 | Hays |
| 5,284,161 A | 2/1994 | Karell |
| 5,313,960 A | 5/1994 | Tomasi |
| 5,316,020 A | 5/1994 | Truffer |
| 5,320,533 A | 6/1994 | Lee |
| 5,336,086 A | 8/1994 | Simmen et al. |
| 5,365,945 A | 11/1994 | Halstrom |
| 5,370,533 A | 12/1994 | Bushnell |
| 5,373,859 A | 12/1994 | Forney |
| 5,392,773 A | 2/1995 | Bertrand |
| 5,409,017 A | 4/1995 | Lowe |
| 5,415,544 A | 5/1995 | Oxman et al. |
| 5,427,117 A | 6/1995 | Thornton |
| 5,456,264 A | 10/1995 | Series et al. |

(56) References Cited

U.S. PATENT DOCUMENTS

| | | |
|---|---|---|
| 5,458,137 A | 10/1995 | Axe et al. |
| 5,474,060 A | 12/1995 | Evans |
| 5,477,850 A | 12/1995 | Zegler et al. |
| 5,499,633 A | 3/1996 | Fenton |
| 5,503,146 A | 4/1996 | Froehlich et al. |
| 5,503,552 A | 4/1996 | Diesso |
| 5,517,983 A | 5/1996 | Deighan et al. |
| 5,537,994 A | 7/1996 | Thornton |
| 5,537,999 A | 7/1996 | Dearman et al. |
| 5,538,000 A | 7/1996 | Rudolph |
| 5,538,014 A | 7/1996 | Wilson et al. |
| 5,540,223 A | 7/1996 | Starr et al. |
| 5,551,419 A | 9/1996 | Froehlich et al. |
| 5,551,872 A | 9/1996 | Mena |
| 5,558,090 A | 9/1996 | James |
| RE35,339 E | 10/1996 | Rapoport |
| 5,560,354 A | 10/1996 | Berthon-Jones et al. |
| 5,562,449 A | 10/1996 | Jacobs et al. |
| 5,566,683 A | 10/1996 | Thornton |
| 5,570,704 A | 11/1996 | Buzzard et al. |
| 5,582,517 A | 12/1996 | Adell |
| 5,592,935 A | 1/1997 | Elstran et al. |
| 5,611,485 A | 3/1997 | Davis |
| 5,657,751 A | 8/1997 | Karr, Jr. |
| 5,657,752 A | 8/1997 | Landis et al. |
| 5,662,101 A | 9/1997 | Ogden et al. |
| 5,676,133 A | 10/1997 | Hickle et al. |
| 5,678,567 A | 10/1997 | Thornton et al. |
| 5,681,164 A | 10/1997 | Bass |
| 5,687,715 A | 11/1997 | Landis et al. |
| 5,713,349 A | 2/1998 | Keaney |
| 5,718,244 A | 2/1998 | Thornton |
| 5,718,500 A | 2/1998 | Vinci guerra et al. |
| 5,720,280 A | 2/1998 | Elstran et al. |
| 5,720,302 A | 2/1998 | Belfer |
| 5,724,965 A | 3/1998 | Handke et al. |
| 5,746,201 A | 5/1998 | Kidd |
| 5,752,510 A | 5/1998 | Goldstein |
| 5,755,219 A | 5/1998 | Thornton |
| 5,807,100 A | 9/1998 | Thornton |
| 5,810,749 A | 9/1998 | Maas |
| 5,829,441 A | 11/1998 | Kidd et al. |
| 5,832,918 A | 11/1998 | Pantino |
| 5,846,082 A | 12/1998 | Thornton |
| 5,887,587 A | 3/1999 | Groenke |
| 5,891,372 A | 4/1999 | Bessett et al. |
| 5,954,048 A * | 9/1999 | Thornton ............... 128/201.18 |
| 5,983,892 A | 11/1999 | Thornton |
| 5,988,166 A | 11/1999 | Hayek |
| 6,012,455 A | 1/2000 | Goldstein |
| 6,012,919 A | 1/2000 | Cross, III |
| 6,083,442 A | 7/2000 | Gabilly |
| 6,109,265 A | 8/2000 | Frantz et al. |
| 6,119,694 A | 9/2000 | Correa et al. |
| 6,123,071 A | 9/2000 | Berthon-Jones et al. |
| 6,155,262 A | 12/2000 | Thornton et al. |
| 6,209,542 B1 | 4/2001 | Thornton |
| 6,247,926 B1 | 6/2001 | Thornton |
| 6,263,871 B1 | 7/2001 | Brown et al. |
| D448,473 S | 9/2001 | Barnett et al. |
| 6,305,376 B1 | 10/2001 | Thornton |
| 6,318,997 B1 | 11/2001 | Mayweather |
| 6,325,064 B1 | 12/2001 | Thornton |
| 6,374,824 B1 | 4/2002 | Thornton |
| 6,405,729 B1 | 6/2002 | Thornton |
| 6,412,488 B1 | 7/2002 | Barnett et al. |
| 6,450,167 B1 | 9/2002 | David et al. |
| 6,464,924 B1 | 10/2002 | Thornton |
| 6,494,206 B1 | 12/2002 | Bergamaschi et al. |
| 6,516,805 B1 | 2/2003 | Thornton |
| 6,536,439 B1 | 3/2003 | Palmisano |
| 6,571,798 B1 | 6/2003 | Thornton |
| 6,604,527 B1 | 8/2003 | Palmisano |
| 6,645,413 B2 | 11/2003 | Jacobs |
| 6,675,802 B1 | 1/2004 | Thornton |
| 6,758,212 B2 | 7/2004 | Swann |
| 6,769,910 B1 | 8/2004 | Pantino |
| 6,845,774 B2 | 1/2005 | Gaskell |
| 6,857,428 B2 | 2/2005 | Thornton |
| 6,877,513 B2 | 4/2005 | Scarberry et al. |
| 7,077,138 B2 | 7/2006 | Bateman et al. |
| 7,174,895 B2 | 2/2007 | Thornton et al. |
| 7,597,103 B2 | 10/2009 | Thornton et al. |
| 7,650,885 B2 | 1/2010 | Paoluccio et al. |
| 7,677,889 B2 | 3/2010 | Thornton |
| 7,721,741 B2 | 5/2010 | Thornton |
| 7,748,386 B2 | 7/2010 | Thornton |
| 7,823,590 B2 | 11/2010 | Bibi et al. |
| 7,832,403 B2 | 11/2010 | Halstrom |
| 7,909,035 B2 | 3/2011 | Thornton |
| 8,020,276 B2 | 9/2011 | Thornton |
| 2002/0000230 A1 | 1/2002 | Gaskell |
| 2002/0129818 A1 | 9/2002 | Morgan et al. |
| 2002/0139366 A1 | 10/2002 | Gaschke |
| 2003/0217753 A1 | 11/2003 | Thornton |
| 2003/0234022 A1 | 12/2003 | Belfer |
| 2004/0079374 A1 | 4/2004 | Thornton |
| 2004/0226563 A1 | 11/2004 | Xu et al. |
| 2004/0237965 A1 | 12/2004 | Bibi et al. |
| 2005/0016544 A1 | 1/2005 | Thornton |
| 2005/0028827 A1 | 2/2005 | Halstrom |
| 2005/0034733 A1 | 2/2005 | Liddle et al. |
| 2005/0268914 A1 | 12/2005 | Paoluccio et al. |
| 2006/0005837 A1 | 1/2006 | Thornton |
| 2006/0124131 A1 | 6/2006 | Chandran et al. |
| 2006/0201520 A1* | 9/2006 | Christensen ............... 128/848 |
| 2007/0125388 A1 | 6/2007 | Thornton et al. |
| 2007/0235037 A1 | 10/2007 | Thornton |
| 2008/0006273 A1 | 1/2008 | Thornton |
| 2008/0006274 A1 | 1/2008 | Thornton |
| 2008/0032256 A1 | 2/2008 | Thornton |
| 2008/0127984 A1 | 6/2008 | Thornton |
| 2008/0295850 A1 | 12/2008 | Lesniak |
| 2009/0130624 A1 | 5/2009 | Sun et al. |
| 2010/0065067 A1 | 3/2010 | Lee |
| 2011/0168187 A1 | 7/2011 | Nelissen |

FOREIGN PATENT DOCUMENTS

| | | | |
|---|---|---|---|
| DE | 35 43 931 A1 | 6/1987 | |
| DE | 37 07 952 | 9/1988 | |
| DE | 37 19 009 | 12/1988 | |
| DE | 29506512.5 | 7/1995 | |
| EP | 0 312 368 A1 | 4/1989 | |
| EP | 0 359 135 A1 | 3/1990 | |
| FR | 2 658 725 A1 | 8/1991 | |
| FR | 2731624 | 9/1996 | ............ A61M 16/06 |
| GB | 1 569 129 | 6/1980 | |
| GB | 2 072 567 A | 10/1981 | |
| WO | WO 91/12777 | 9/1991 | |
| WO | WO 97/25010 | 7/1997 | |
| WO | WO 98/26736 | 6/1998 | |
| WO | WO 98/46177 | 10/1998 | |

OTHER PUBLICATIONS

Samuel T. Kuna, M.D., et al., "Effect of Progressive Mandibular Advancement on Pharyngeal Airway Size in Anesthetized Adults," National Institute of Health; NIH Public Access Author Manuscript; Published Oct. 2008; Anesthesiology; 109(4); 16 pages, Oct. 2008.

Canadian Intellectual Property Office, Application No. 2,502,280, Applicant: W. Keith Thornton, 3 pages, dated Feb. 23, 2010.

Personally Moulded Sleep Apnea Masks, http:/;web.archive.org/web/20030618145716/www.sleepapneamasks.com.au/default.asp, downloaded Aug. 17, 2009 (2 pages).

European Patent Office, Application No. 03 809 555.0-125, Applicant: W. Keith Thornton, 3 pages, dated Feb. 23, 2010; 4 pages.

PCT, Notification of Transmittal of the International Search Report and the Written Opinion of the International Searching Authority, or the Declaration, International Application No. PCT/US2011/039231, filing date Jun. 6, 2011 (11 pgs).

(56) References Cited

OTHER PUBLICATIONS

PCT, Notification of Transmittal of the International Search Report and the Written Opinion of the International Searching Authority, or the Declaration, PCT/US2010/051136, 10 pages, Mar. 4, 2011.
Japanese Patent Office re patent application 2004-500750, mailed Oct. 14, 2008.
Australian Office Action re patent application No. 2007/243957 dated Mar. 9, 2012.
PCT Intl. Searching Authority, Invitation to pay Add'l Fees, Re PCT/US2012/028885 mailed May 30, 2012 (0306 Foreign).
PCT Intl. Searching Authority, Invitation to pay Add'l Fees, Re PCT/US2012/032407 mailed May 30, 2012.
Canadian IPO patent application No. 2,502,280 dated Feb. 23, 2010.
PCT Notification of Transmittal of the International Search Report and the Written Opinion of the International Searching Authority, or the Declaration; mailed Jul. 13, 2012; International app No. PCT/US2012/032407; 18 pages.
Mayo Clinic Health Letter; Reliable Information for a Healthier Life; *Snoring: Laser Surgery Joins Battle to Restore Peace and Quiet*; vol. 13, No. 7, 8 pages, Jul. 1995.
Photocopies of 2-piece dental device manufactured by Currie-Gibson Dental Lboratory, Inc., prior to Apr. 13, 1993, 5 pages.
Farrar, et al, *A Clinical Outline of Temporomandibular Joint Diagnosis and Treatment*, Normandie Study Group for TMJ Dysfunction, 3 pages, 1983.
Schmidt-Nowara, etal.; An American Sleep Disorders Association Review; *Oral Appliances for the Treatment of Snoring and Obstructive Sleep Apnea: A Review*; pp. 501-510, 1995.
George, Peter; *Treatment of Snoring and Obstructive Sleep Apnea with a Dental Device*; 5 pages, Jul.-Aug. 1993.
Database WOI, Section PQ, Week 9039, Derwent Publications, Ltd., London, GB; XP-002116355 Abstract—*Surgical Mouth Air Duct*; 1 page, Dec. 15, 1989.
PCT Notification of Transmittal of the International Search Report or the Declaration for International Application No. PCT/US97/08708, 4 pages, Aug. 12, 1997.
PCT Invitation to Pay Additional Fees for International Application No. PCT/US03/13705, 6 pages, Oct. 10, 2003.
PCT International Search Report and Written Opinion, International Application No. PCT/US06/26622, 11 pages, Feb. 21, 2007.
"Donning the Mask," Dräger: X-plore 5500.2006.Dräger Safety, http://www.draeger-usa.com/ST/internet/pdf/US/protection/AnlegiPO_X-plore_5500_US.pdf, 2 pages, Accessed Sep. 14, 2006.
PCT, Notification of Transmittal of the International Search Report and the Written Opinion of the International Searching Authority, or the Declaration, PCT/US07/02736, 10 pages, Date Mailed Oct. 26, 2007.
Thornton, "Oral Appliance for Treating a Breathing Condition," U.S. Appl. No. 11/278,918, pending, 42 pages, filed Apr. 6, 2006.
W. Keith Thornton, "Multi-Chamber Mask and Method of Forming the Same," U.S. Appl. No. 11/428,933, filed Jul. 6, 2006.
W. Keith Thornton, "Stability Medical Mask," U.S. Appl. No. 11/853,343, currently pending, filed Sep. 11, 2007.
W. Keith Thornton, "System and Method for Custom-Orientihng a Medical Mask to an Oral Appliance," U.S. Appl. No. 11/947,291, currently pending, filed Nov. 29, 2007.
PCT, Notification of Transmittal of the International Search Report and the Written Opinion of the International Searching Authority, or the Declaration, PCT/US06/26622, 11 pages, Date Mailed: Feb. 21, 2007.

\* cited by examiner

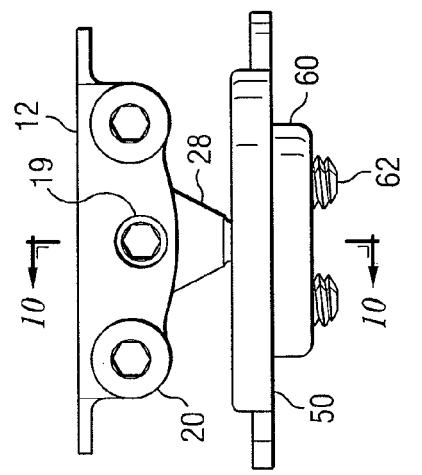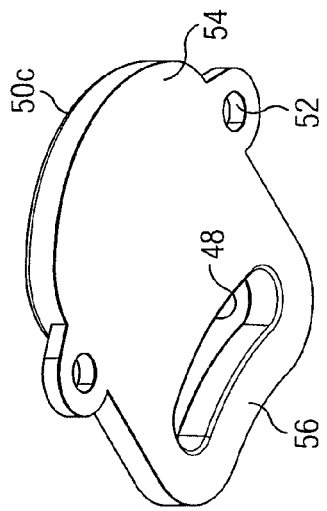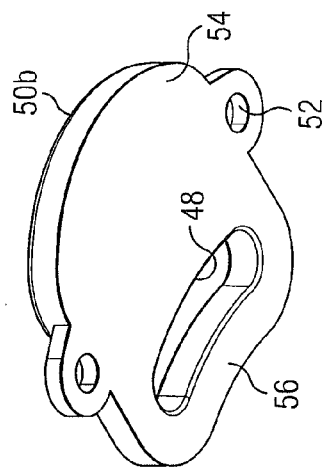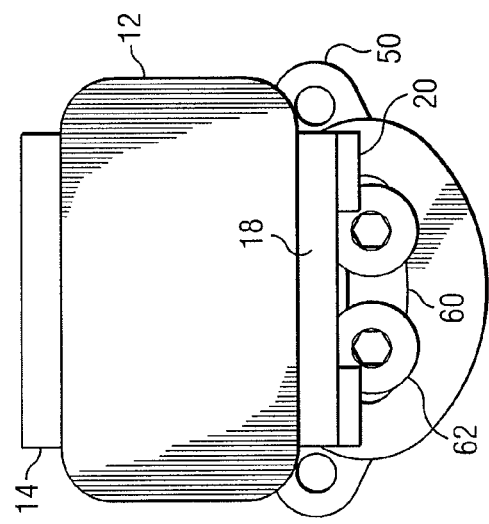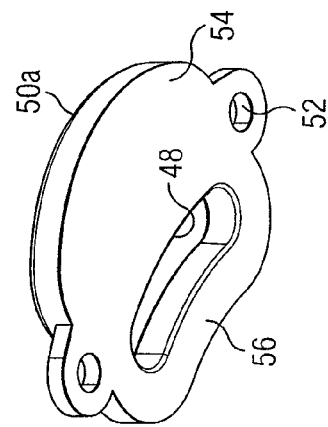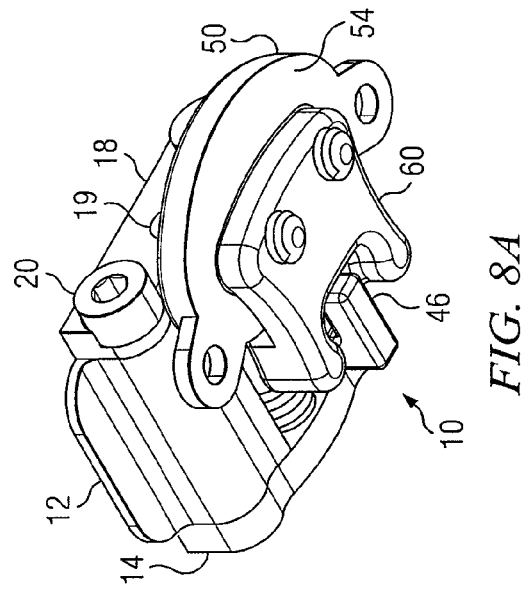

APPARATUS AND METHOD FOR COUPLING AN ORAL APPLIANCE TO A GAS DELIVERY DEVICE

RELATED APPLICATIONS

This application claims the benefit under 35 U.S.C. §119 (e) of U.S. Provisional Application Ser. No. 61/156,323 filed Feb. 27, 2009.

TECHNICAL FIELD OF THE INVENTION

This disclosure relates generally to oral appliances, and more particularly to an apparatus and method for coupling an oral appliance to a gas delivery device.

BACKGROUND OF THE INVENTION

Many people experience breathing problems, which may result in difficulty sleeping, in snoring, or in other more serious conditions such as obstructive sleep apnea. One treatment for such breathing disorders involves the use of devices that are inserted into a user's mouth for extending the user's lower jaw forward. These devices open the airway (i.e., breathing passageway) more fully to allow easier breathing through the nose and mouth. Certain of these devices include upper and lower arches that are connected together using a mechanism that may be adjusted to pull the lower arch, and thus the user's lower jaw, forward to open the airway more fully. Certain devices include masks that deliver air, oxygen, or other gases to a user through their mouth and/or nasal passages.

SUMMARY OF THE INVENTION

According to one embodiment, an apparatus for improved breathing includes an oral appliance, a gas delivery device, and a coupler. The gas delivery device is configured to direct gas to the breathing passages of a user. The coupler includes a swivel, a clamp, and a post with two arms. The clamp is configured to engage the post and to slide along the length of the post. The clamp is also configured to position and secure the swivel to define its position and orientation relative to the post. The gas delivery device is coupled to the oral appliance utilizing the swivel.

According to one embodiment, an apparatus for coupling an oral appliance to a gas delivery device includes a post, a swivel, and first and second opposing clamps. The post includes a base configured to couple to the oral appliance; a first arm extending from the base and defining a channel extending along a portion of the first arm; and a second arm extending from the base, extending substantially parallel to the first arm, the second arm defining a channel extending along a portion of the second arm. The swivel is substantially spherical and is configured to position the gas delivery device. The first clamp is configured to engage and slide along the channel defined by the first arm and the second clamp is configured to engage and slide along the channel defined by the second arm. The first and second opposing clamps are together configured to position and secure the location and orientation of the swivel relative to the post. In certain embodiments, the first and second opposing clamps may include protrusions shaped to engage and slide along the channels defined by the first and second arms.

According to one embodiment, a method for coupling an oral appliance to a gas delivery device includes coupling the gas delivery device to the oral appliance using a coupler. The coupler includes a post, a first clamp, a second clamp, and a substantially spherical swivel. The post includes a base, a first arm extending from the base, a second arm extending from the base. The first arm defines a first channel extending along a portion of the first arm. The second arm extends substantially parallel to the first arm and defines a second channel extending along a portion of the second arm. The first clamp is configured to engage and slide along the first channel and the second clamp is configured to engage and slide along the second channel. The method includes positioning the gas delivery device relative to the oral appliance. Positioning the gas delivery device includes adjusting the location of the gas delivery device along the first and second channels utilizing the first and second clamps. Positioning the gas delivery device also includes adjusting the orientation of the gas delivery device utilizing the swivel. The method further includes securing the position of the gas delivery device relative to the oral appliance utilizing the first and second clamps.

Certain embodiments of the present invention may provide one or more technical advantages For example, certain embodiments may provide for precise positioning of a gas delivery device. As another example, certain embodiments may provide for coupling a gas delivery device to an oral appliance in a manner that allows for positioning of the gas delivery device as well as adjustment of the oral appliance. Certain embodiments may provide some, none, or all of these advantages. Certain embodiments may provide one or more other technical advantages, one or more of which may be readily apparent to those skilled in the art from the figures, description, and claims included herein.

BRIEF DESCRIPTION OF THE DRAWINGS

Reference is now made to the following description taken in conjunction with the accompanying drawings, wherein like reference numbers represent like parts, in which:

FIGS. 7A through 7C illustrate example receivers with varying dimensions;

DETAILED DESCRIPTION OF THE INVENTION

Figure 1:
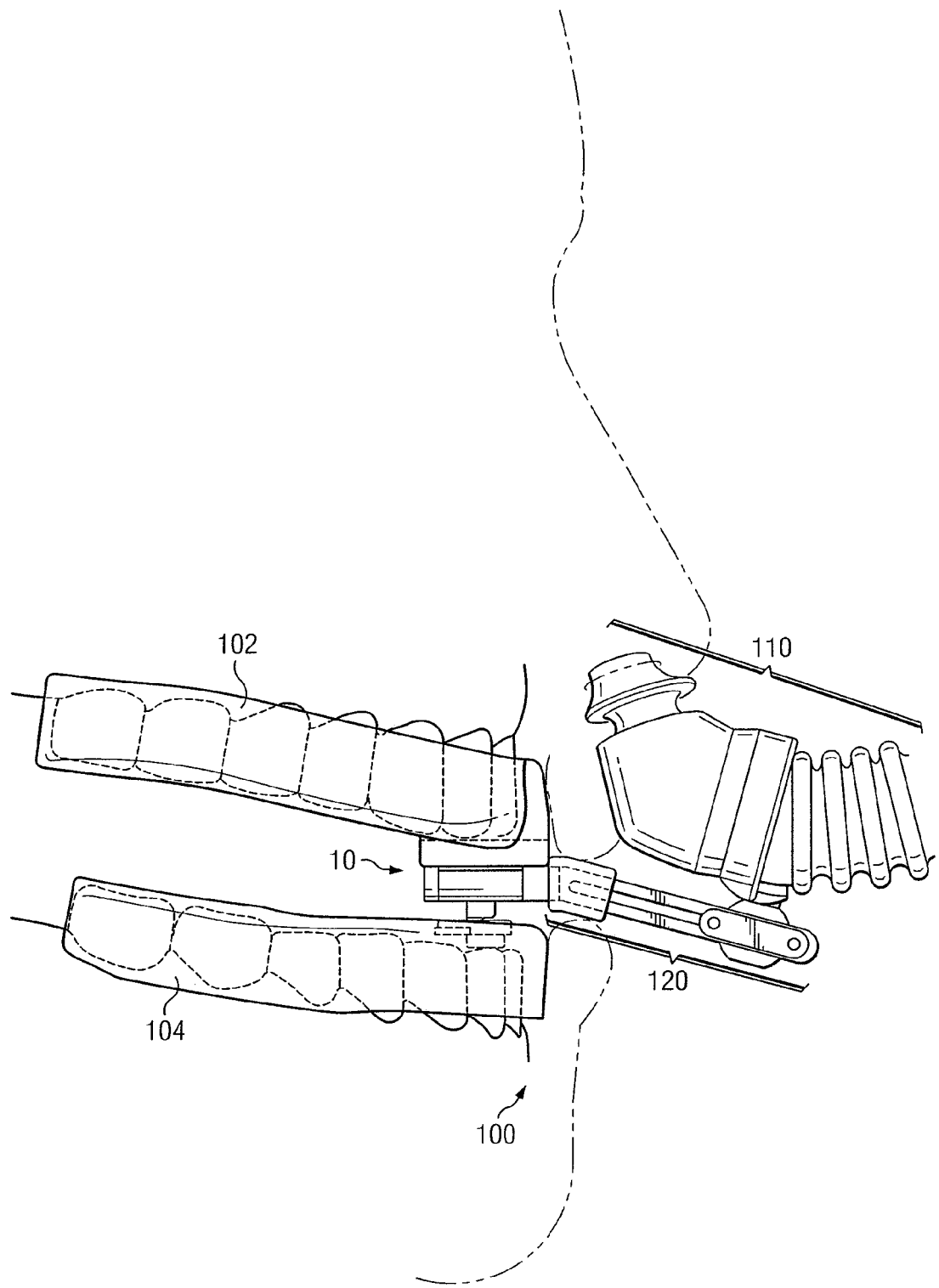
FIG. 1 illustrates an example oral appliance for improving a user's breathing.
Figure 2A:
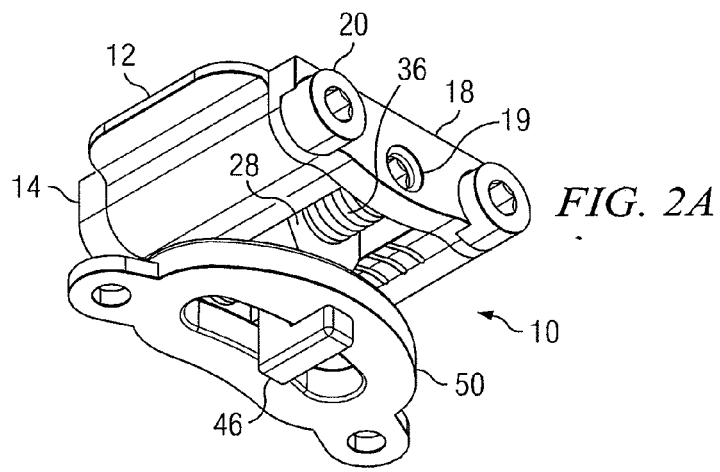
FIGS. 2A through 5B illustrate an example adjustment mechanism.
Figure 2B:
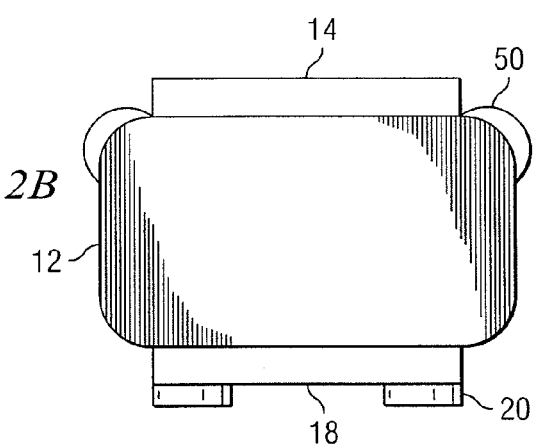
Figure 2C:
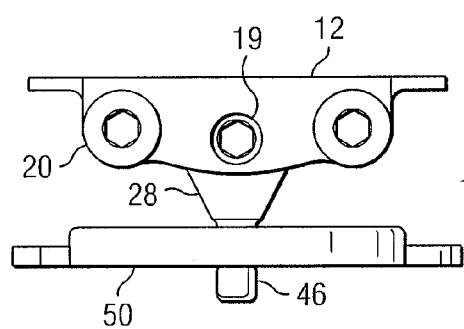
Figure 2D:
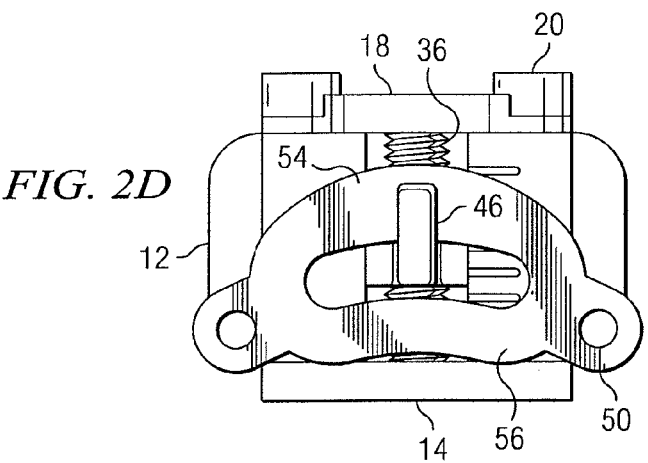
Figure 3:
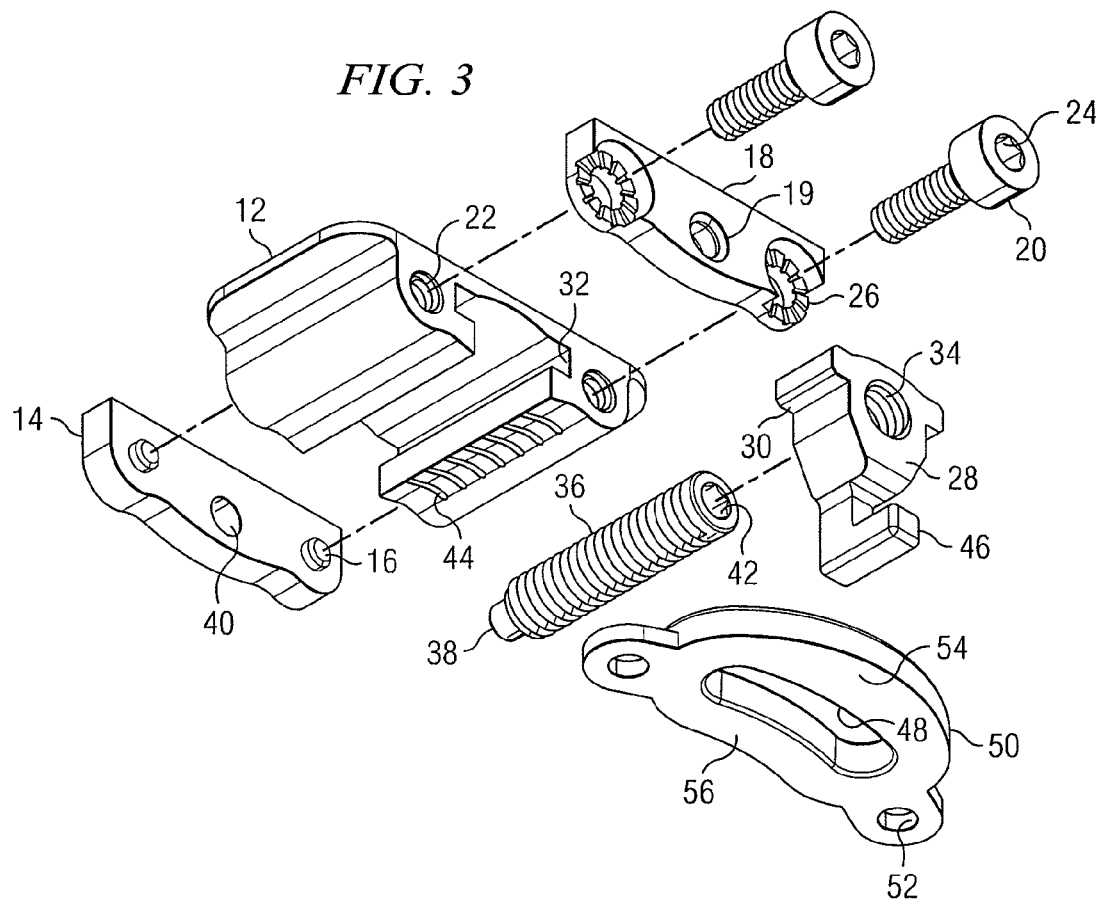
Figure 4A:
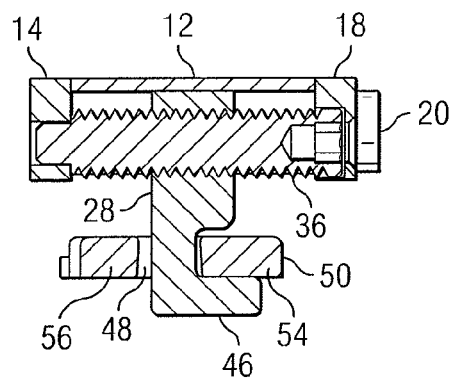
Figure 4B:
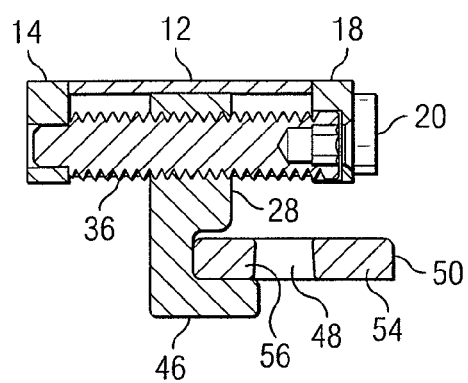
Figure 5A:
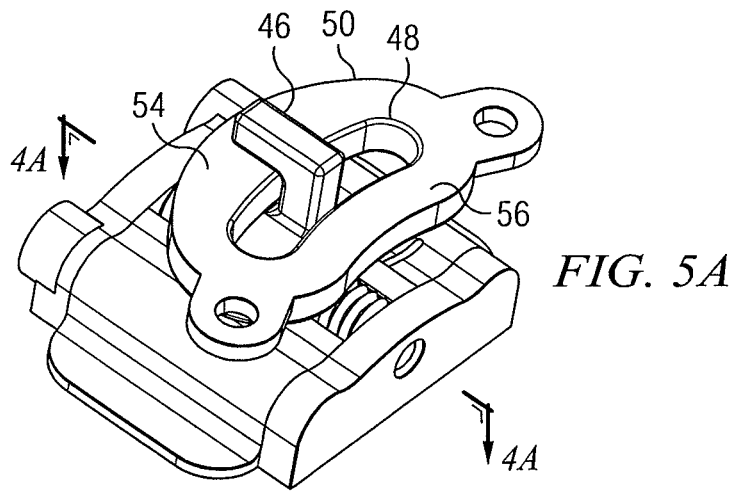
Figure 5B:
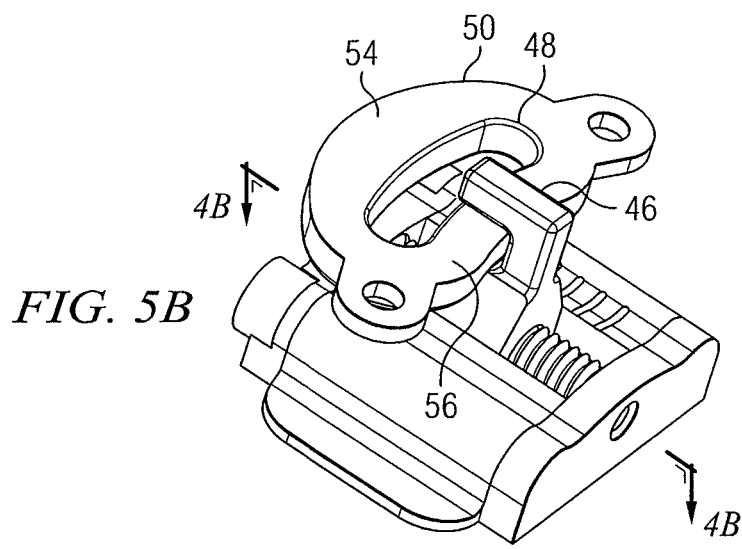

FIG. 1 illustrates an example oral appliance 100 coupled to an example gas delivery device 110. In general, oral appliance 100 may be used to treat sleep disordered breathing, such as snoring or obstructive sleep apnea, through forward adjustment of the user's lower jaw relative to the upper jaw. This forward adjustment opens the breathing passage more fully and facilitates improved breathing through the user's nose and mouth. In certain embodiments, oral appliance 100 remains entirely within the user's mouth and surfaces of oral appliance 100 that may contact the interior of the user's mouth are smooth to prevent injury or discomfort. Although not intended to be exclusive, example oral appliances are described in one or more of U.S. Pat. Nos. 5,427,117; 5,566, 683; 5,755,219; 6,516,805; 5,954,048; 5,983,892; 6,374,824; 6,325,064; 6,247,926; and 6,405,729 each of which is incorporated herein by reference.

Oral appliance 100 includes an upper arch 102 configured to receive at least some of a user's upper teeth, a lower arch 104 configured to receive at least some of the user's lower teeth, and an adjustment mechanism 10. Upper arch 102 and lower arch 104 may include molds of at least some of the user's upper and lower teeth, respectively, for improved performance and comfort. Adjustment mechanism 10 couples lower arch 104 to upper arch 102 and may be adjusted to pull lower arch 104 forward to facilitate improved breathing. In certain embodiments, adjustment mechanism 10 may also vertically position lower arch 104 relative to upper arch 102 to determine the opening of the user's lower jaw. The components of adjustment mechanism 10 may be made from any suitable material such as, for example, a biocompatible metal or hard plastic.

Gas delivery device 110 may fit over the patient's nose and other portions of the patient's face or may be nasal inserts or nose pillows to direct gas directly into the patient's nasal passages. Although not intended to be exclusive, example gas delivery devices are described in one or more of U.S. Patent Publication Nos. 2007/0006879; 2008/0006273; and 2008/0060648 each of which is incorporated herein by reference. Gas delivery device 110 may be coupled to a system for providing one or more gases. For example, gas delivery device 110 may be coupled to a positive air pressure device, such as a constant positive air pressure (CPAP) system or bi-level positive air pressure (BiPAP) system. Although CPAP and BiPAP are used as examples, other systems for delivering air or other gases at constant or varying pressure may be used. Such systems may deliver any breathable gas, such as air or oxygen. It should be understood that the term "gas" is intended to include air.

Coupler 120 may couple oral appliance 100 to gas delivery device 110. Coupler 120 allows for adjustable movement of gas delivery device 110 relative to oral appliance 100 in multiple directions. In particular embodiments, coupler 120 allows gas delivery device 110 to be adjusted along a substantially anterior-posterior axis and rotated about multiple axes.

FIGS. 2A through 5B illustrate an example adjustment mechanism 10 for use with oral appliance 100. In certain embodiments, adjustment mechanism 10 may include body 12, hook 28, adjustor 36, and receiver 50. Body 12 may be integrated into or coupled to upper arch 102. Body 12 may include a rear plate 14, one or more rear fasteners 16, a front plate 18, and one or more front fasteners 20. In certain embodiments, body 12 may further include one or more fastener passages 22, one or more guides 32, and one or more adjustment indicators 44. Hook 28 may include flange 30, adjustor passage 34, and arm 46.

When assembled, rear plate 14 may be coupled to body 12 through the use of one or more fasteners 16. Fasteners 16 may be threaded fasteners, pins, or any other appropriate fastener to couple rear plate 14 to body 12. Hook 28 may be coupled to body 12 through the use of one or more flanges 30 engaged within the one or more guides 32. Adjustor 36 may include pin 38 and opening 42. Opening 42 may be square, hexagonal, or any other appropriate shape to allow for a rotational force to be applied to adjustor 36. Adjustor 36 may be positioned within adjustor passage 34 of hook 28 and pin 38 may be aligned with and inserted into hole 40 of rear plate 14. Front plate 18 may be coupled to body 12 through the use of one or more fasteners 20. Fasteners 20 may include threaded fasteners, pins, or any other appropriate fastener to couple front plate 18 to body 12. In certain embodiments, front plate 18 may include one or more structures to lock or secure one or more fasteners 20. For example, in embodiments utilizing a threaded fastener 20 as shown, front plate 18 may include one or more grooves and associated projections 26 to better secure fastener 20 in place.

In certain embodiments, front plate 18 may include an opening 19 that substantially aligns with opening 42 of adjustor 36. In operation, opening 19 may provide access to opening 42 of adjustor 36 for locational adjustment of hook 28. In certain embodiments, adjustor 36 may be threaded and may engage cooperative threads of adjustor passage 34 of hook 28 such that rotation of adjustor 36 moves hook 28 forward or rearward relative to body 12.

Receiver 50 is configured to receive arm 46 of hook 28 such that forward adjustment of hook 28 pulls lower arch 104 forward. Receiver 50 may be fully integrated into, permanently coupled to, or separate and removable from lower arch 104. In certain embodiments, receiver 50 may include one or more openings 52 that may be used to couple receiver 50 to lower arch 104 through the use of any appropriate fastener. In certain embodiments, receiver 50 may also include slot 48 separating front shelf 54 from rear shelf 56. In operation, hook 28 may engage either front shelf 54 or rear shelf 56. In certain embodiments, the use of rear shelf 56 may provide additional extension of lower arch 104 in the forward direction relative to the use of front shelf 54.

Receiver 50 may be modified according to particular needs to provide increased flexibility. For example, the vertical location of front shelf 54 and/or rear shelf 56 relative to lower arch 104 may be adjusted or otherwise modified, either during or after initial construction of receiver 50. As another example, receivers 50 with varying vertical dimensions may be provided, such that the use of a particular receiver 50 may be selected to define a prescribed vertical separation between upper arch 102 and lower arch 104 and thus a prescribed opening of the user's lower jaw. As another example, the vertical location of front shelf 54 and/or rear shelf 56 may be selected by coupling receiver 50 to lower arch 104 in either of two possible orientations (i.e., with a particular horizontal surface facing up or facing down). As another example, receivers 50 with varying horizontal dimensions may be provided, such that the use of a particular receiver 50 may be selected to define a prescribed forward location (or range of locations) for lower arch 104 relative to upper arch 102.

Slot 48 may allow horizontal movement of lower arch 104 relative to upper arch 102 when lower arch 104 is coupled to upper arch 102. Similarly, the posterior surface of front shelf 54 and/or rear shelf 56 may be shaped to guide the horizontal movement of lower arch 104 relative to upper arch 102 in an arc-shaped or other desirable path.

Figure 6A:
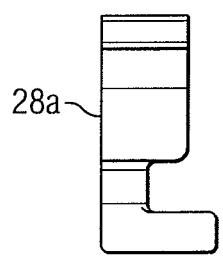
FIGS. 6A through 6C illustrate example hooks with varying lengths, for use with an example adjustment mechanism.
Figure 6B:
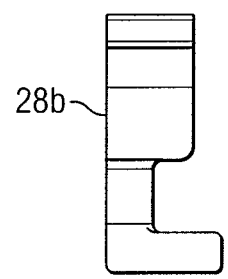
Figure 6C:
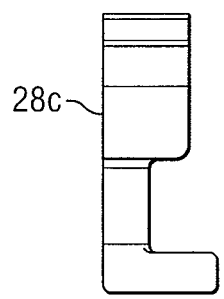
Figure 8D:
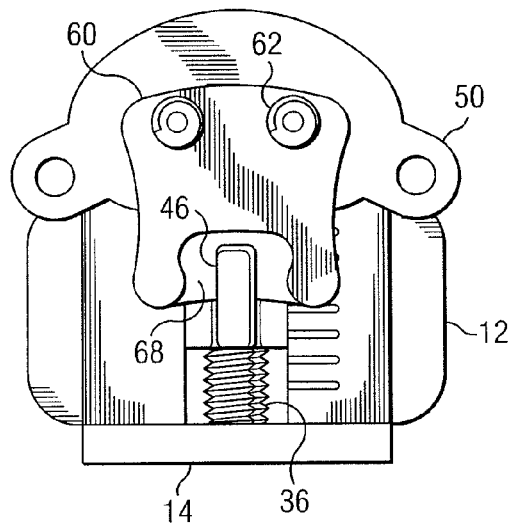
FIGS. 8A through 10 illustrate an example adjustment mechanism utilizing an example extender.
Figure 9:
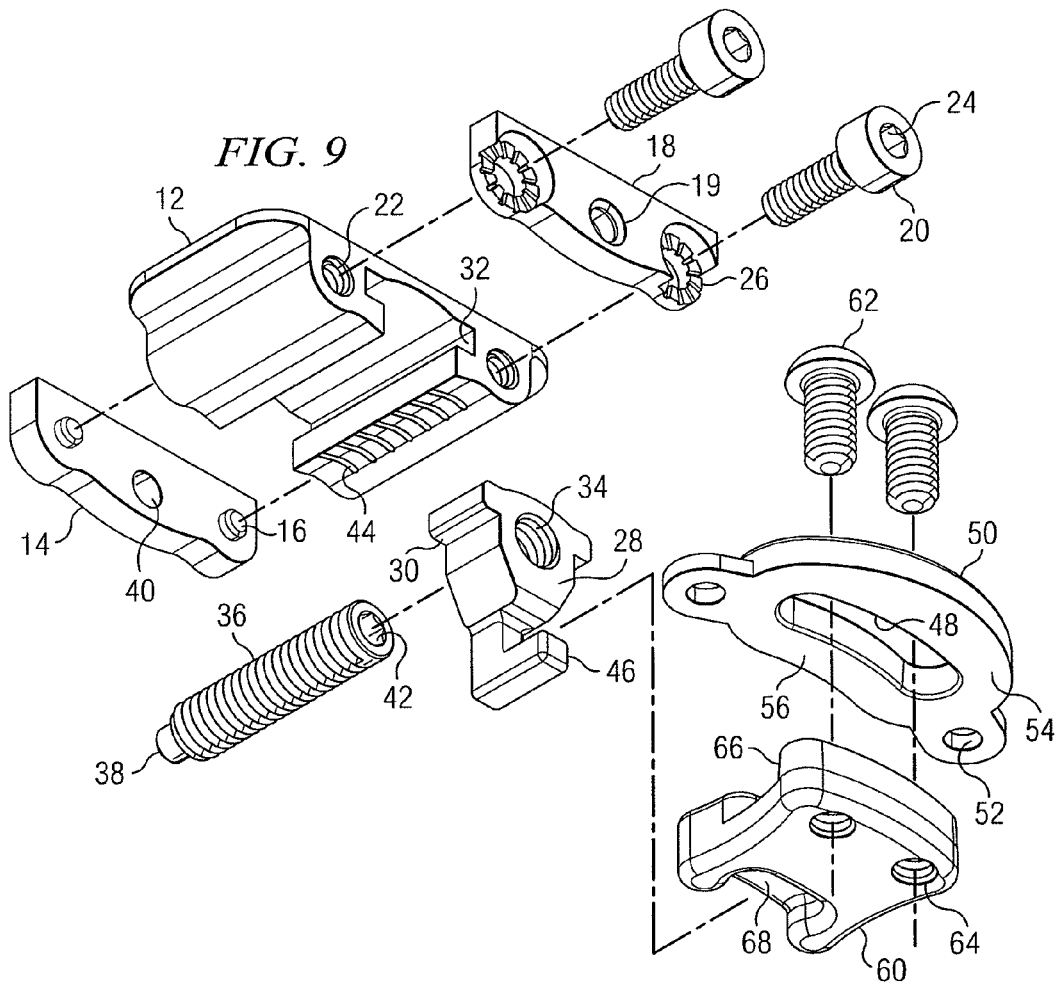
Figure 10:
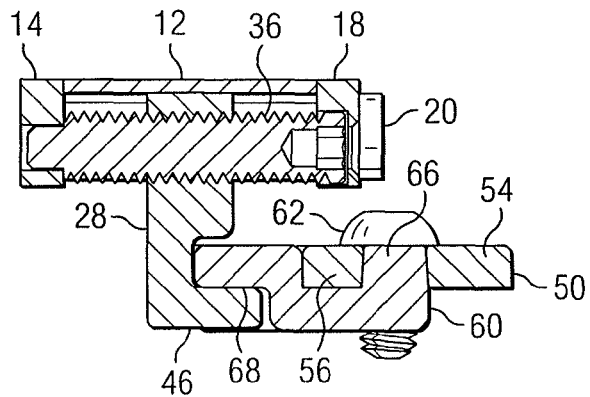

FIGS. 6A through 6C illustrate example hooks 28 with varying lengths, for use with adjustment mechanism 10. In operation, the use of a particular hook 28 may be selected to define a prescribed vertical separation between upper arch 102 and lower arch 104 and thus a prescribed opening of the user's lower jaw. For example, in the embodiments shown, the use of hook 28c may allow for greater vertical separation between upper arch 102 and lower arch 104 than the vertical separation allowed with the use of hooks 28a or 28b. In particular embodiments, the use of hooks 28 with varying lengths, together with the use of receivers 50 with varying vertical dimensions, may provide an increased range and/or precision for selection of a prescribed opening of the user's lower jaw.

FIGS. 7A through 7C illustrate example receivers with varying dimensions, for use with adjustment mechanism 10. In operation, the use of a particular receiver may be selected to define a prescribed forward location (or range of forward locations) for lower arch 104 relative to upper arch 102 and thus a prescribed forward location (or range of forward locations) for the user's lower jaw. For example, in the embodiments shown, the use of receiver 50c may allow for lower arch 104 to be positioned further forward with respect to upper arch 102 than with the use of receivers 50a or 50b. In particular embodiments, the use of receivers 50 with varying dimensions may provide an increased range and/or precision for adjusting the forward location of lower arch 104 relative to upper arch 102.

FIGS. 8A through 10 illustrate an example adjustment mechanism 10 utilizing an example extender 60. In certain embodiments, extender 60 couples to receiver 50 and operates to receive arm 46 of hook 28 such that the forward positioning of lower arch 104 is greater than that provided without extender 60.

Figure 11A:
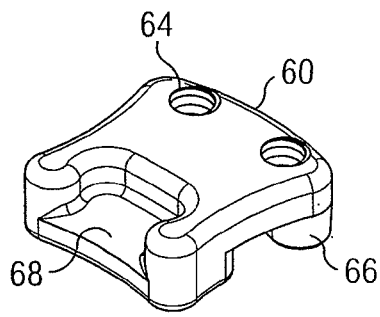
FIGS. 11A and 11B illustrate an example extender.
Figure 11B:
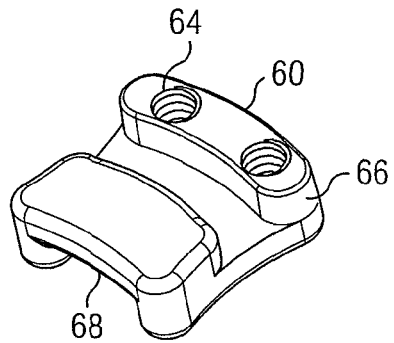

FIGS. 11A and 11B illustrate an example extender 60 for use with an example adjustment mechanism 10. In certain embodiments, extender 60 may include a shelf 68 that engages arm 46 of hook 28. In certain embodiments, extender 60 may also include one or more projections 66 that may cooperatively engage slot 48 of receiver 50. In certain embodiments, extender 60 may also include one or more openings 64 that may cooperate with one or more fasteners 62 to couple extender 60 to receiver 50, such as via slot 48. Fastener 62 may be a threaded fastener, pin, or any other appropriate fastener for coupling extender 60 to receiver 50.

Figure 12A:
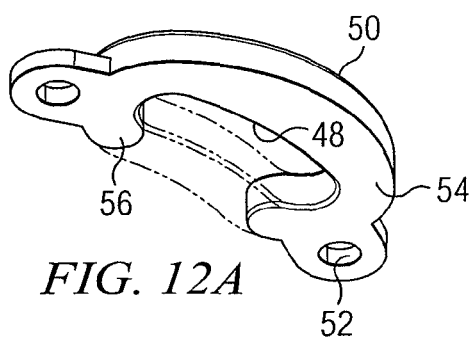
FIGS. 12A and 12B illustrate example receivers.
Figure 12B:
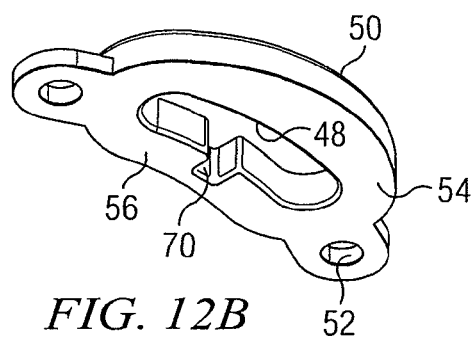

FIGS. 12A and 12B illustrate example receivers 50 for use with example adjustment mechanisms 10. As shown in FIG. 12A, in certain embodiments, receiver 50 may include only a single shelf 54, in which case slot 48 may be fully or partially exposed in the rearward direction. As shown in FIG. 12B, receiver 50 may include notch 70 in slot 48. In operation, the use of receiver 50 including only a single shelf 54 or including notch 70 may allow hook 28 to engage or disengage from shelf 54 of receiver 50 after oral appliance 100 has been inserted into a user's mouth.

Figure 13:
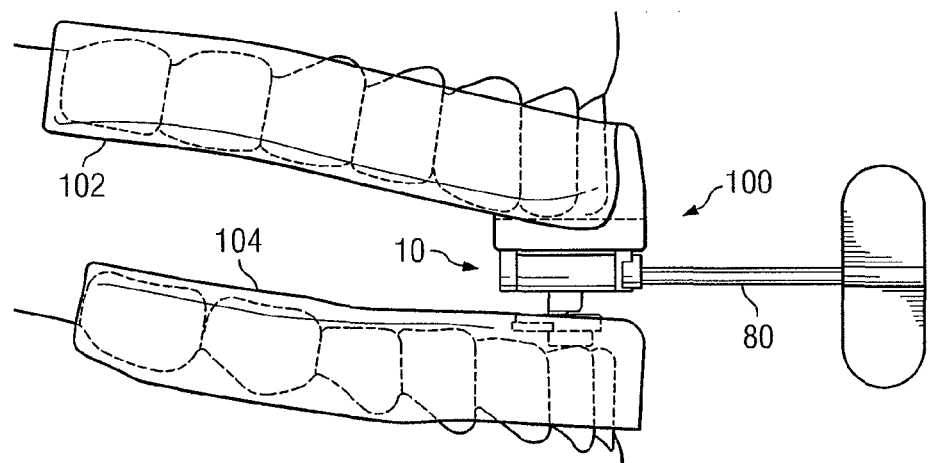
FIGS. 13 through 16 illustrate an example adjustment mechanism utilizing an example adjustment key.

FIG. 13 illustrates an example oral appliance 100 with an example adjustment key 80. Adjustment key 80 may have a cross-section that is hexagonal, square, or any other appropriate shape. In certain embodiments, adjustment key 80 may be used to exert a rotational force on adjustor 36 causing adjustor 36 to turn and thereby provide adjustment of hook 28, forward or rearward.

Figure 15:
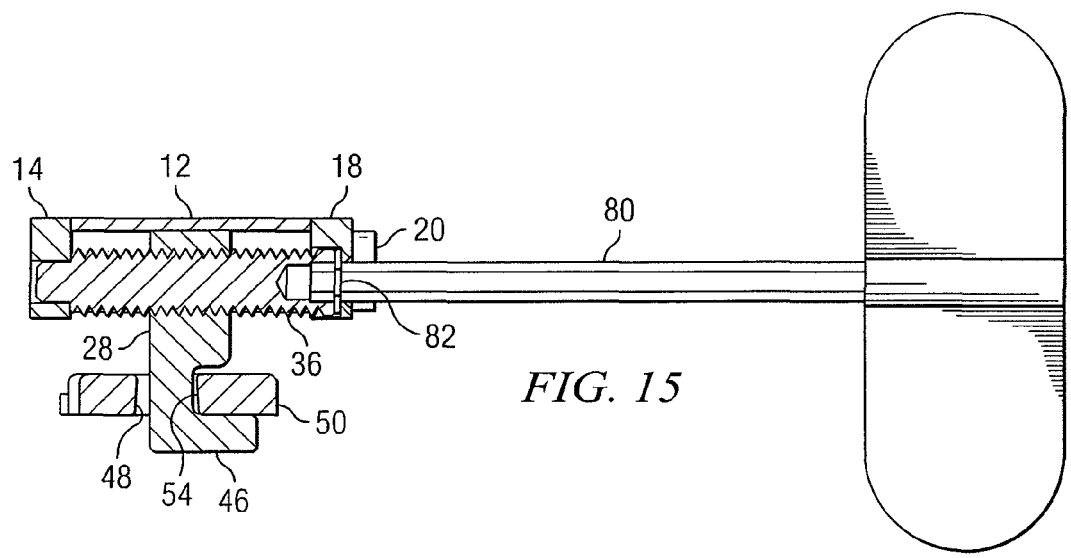
Figure 14:
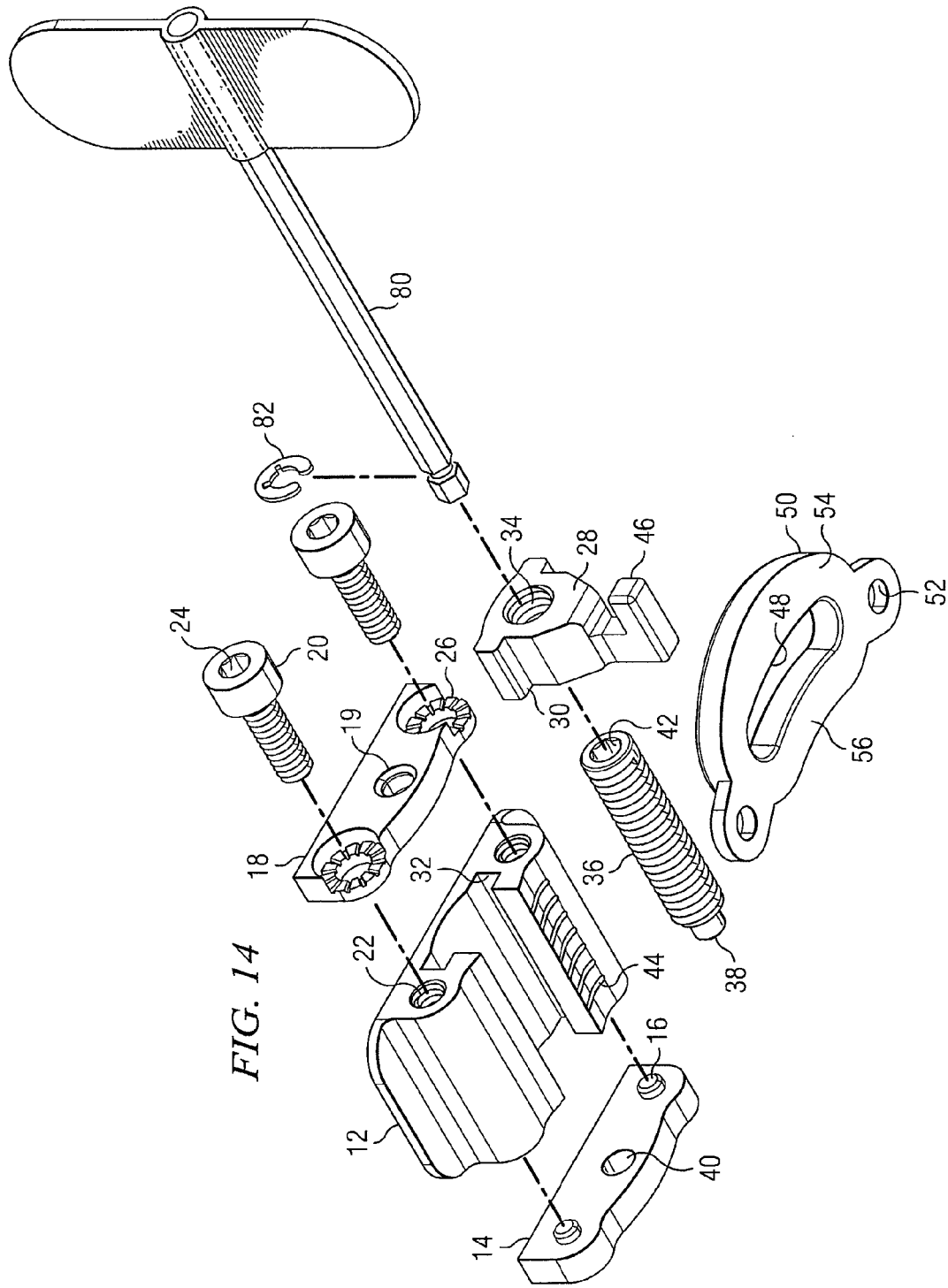
Figure 16:
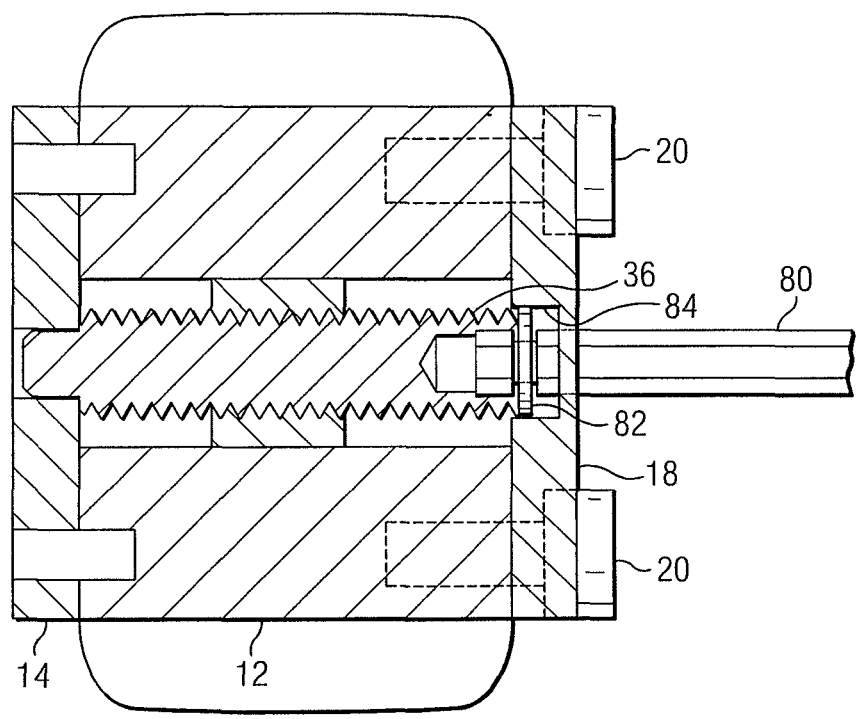
Figure 17:
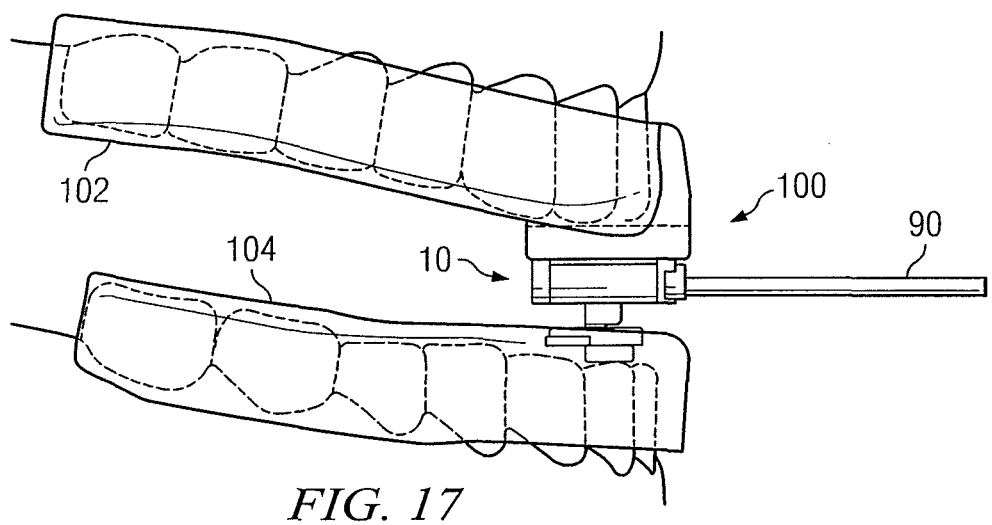
FIGS. 17 through 19B illustrate an example adjustment mechanism utilizing an example extension post.
Figure 18:
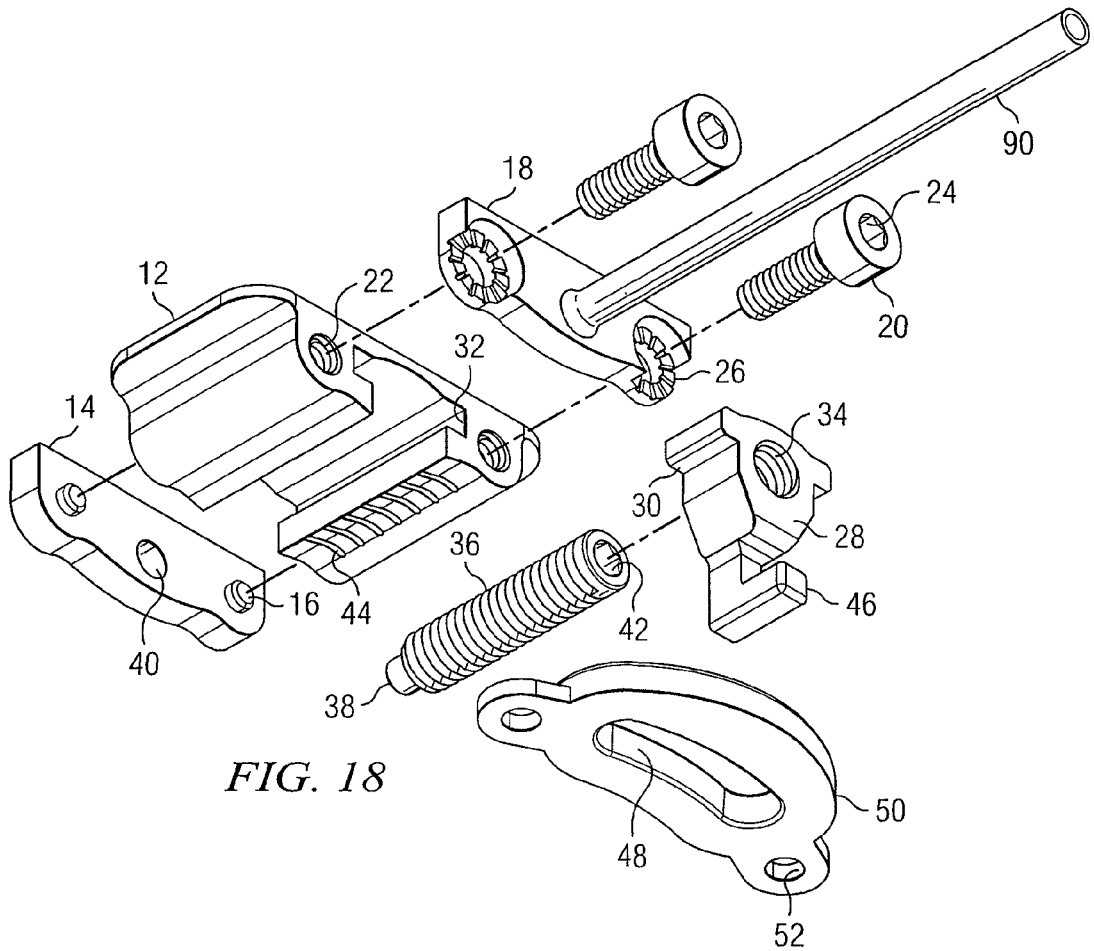

FIGS. 14 through 16 illustrate example adjustment mechanisms 10 utilizing example adjustment keys 80. In certain embodiments, adjustment key 80 may be coupled to adjustment mechanism 10 through the use of retainer ring 82 and notch 84. In operation, retainer ring 82 may engage notch 84, thus preventing removal of adjustment key 80. In operation, embodiments of adjustment mechanism 10 including adjustment key 80 and retaining ring 82 may be used by a particular user during a trial period for oral appliance 100. During this trial period, the user and/or a clinician may make periodic adjustments to adjustment mechanism 10 through the use of adjustment key 80 to achieve the desired positioning of lower arch 104 relative to upper arch 102. In these embodiments, once the desired positioning has been achieved, adjustment key 80 and retaining ring 82 may be removed. In these embodiments, once the desired positioning has been achieved, front plate 18 may be replaced with a front plate 18 that does not include an opening 19.

FIGS. 17 through 19B illustrate an example oral appliance 100 with an example extension post 90. Extension post 90 may be formed of any suitable material, such as a metal or hard plastic. In certain embodiments, extension post 90 may be used to couple oral appliance 100 to one or more other devices and/or to orient one or more other devices relative to oral appliance 100. For example, extension post 90 may be used to couple oral appliance 100 to a venting seal or a gas delivery device, such as a face mask or a nose mask. In a particular embodiment, extension post may be used to couple oral appliance 100 to a mask associated with a continuous positive airway pressure (CPAP) system.

In certain embodiments, extension post 90 may be substantially rigid, to provide for sufficiently precise positioning of one or more devices relative to upper arch 102. For example, in certain embodiments, extension post 90 may be used to provide substantially precise and repeatable positioning of a face mask or nose mask relative to upper arch 102. The length of extension post 90 may vary depending upon its intended use. For example, extension post 90 may be substantially shorter if it is intended to be used to couple a venting seal to oral appliance 100 than if it is intended to couple a nose mask to oral appliance 100. The invention contemplates any reasonable length of extension post 90, so long as the length is appropriate to perform the intended function.

Figure 19A:
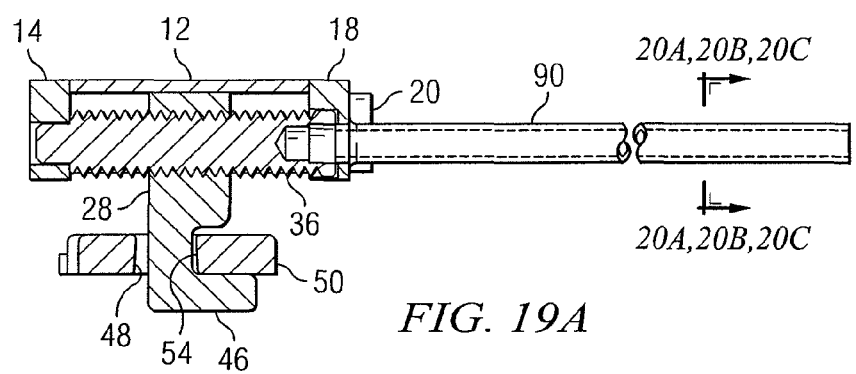
Figure 19B:
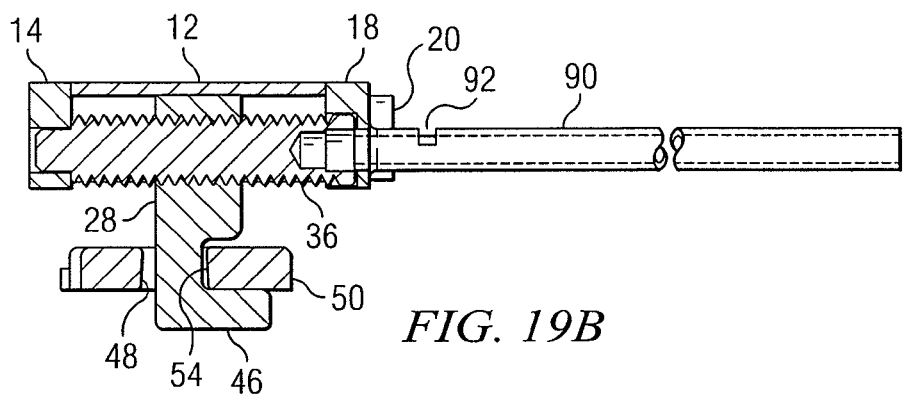

In certain embodiments, extension post 90 may include one or more features that can operate to index or assist in securing one or more devices to extension post 90. For example, as shown in FIG. 19B, extension post 90 may include one or more locators 92 at one or more positions along the length of extension post 90. In operation, a device coupled to or guided by extension post 90 may include one or more structures that can cooperate with the one or more locators 92 to index or assist in securing the device. In the embodiment shown, locator 92 is in the form of a notch, however, in alternative embodiments, locator 92 may be in the form of a ridge, protrusion, or any other appropriate shape or structure. In particular embodiments, the position of locator 92 may be adjustable.

In certain embodiments, extension post 90 may be coupled to front plate 18. In these embodiments, extension post 90 may be coupled through the use of any appropriate means, such as welding or threaded coupling. In alternative embodiments, extension post 90 may be integrally formed with front plate 18. In certain embodiments, extension post 90 may be substantially hollow and may couple to front plate 18 such that the hollow interior of extension post 90 substantially aligns with an opening 19. In operation, the hollow portion of extension post 90 may provide access to adjustor 36 through opening 19. The cross-sectional shape of extension post 90 may take any appropriate form, so long as it remains reasonable for the intended function.

Figure 20A:
FIGS. 20A through 20B illustrate transverse cross-sectional views of example extension posts.
Figure 20B:
Figure 20C:

FIGS. 20A through 20C illustrate transverse cross-sectional views of example extension posts 90. As shown, extension post 90 may have a cross sectional shape that is a circle, oval, or diamond. In certain embodiments, non-circular cross-sections may function to more precisely position a device coupled to oral-appliance 100 through the use of extension post 90, by substantially limiting the likelihood that the device will rotate about the extension post 90.

In certain embodiments, receiver 50 may be removable. For example, lower arch 104 may include a recess that allows receiver 50 to be positioned within, and then removed from, lower arch 104. In embodiments including a removable receiver 50 and a recess in lower arch 104, the recess may be integrally formed in lower arch 104. In alternative embodiments, the recess may be formed in or by a housing that is included in lower arch 104.

Figure 21:
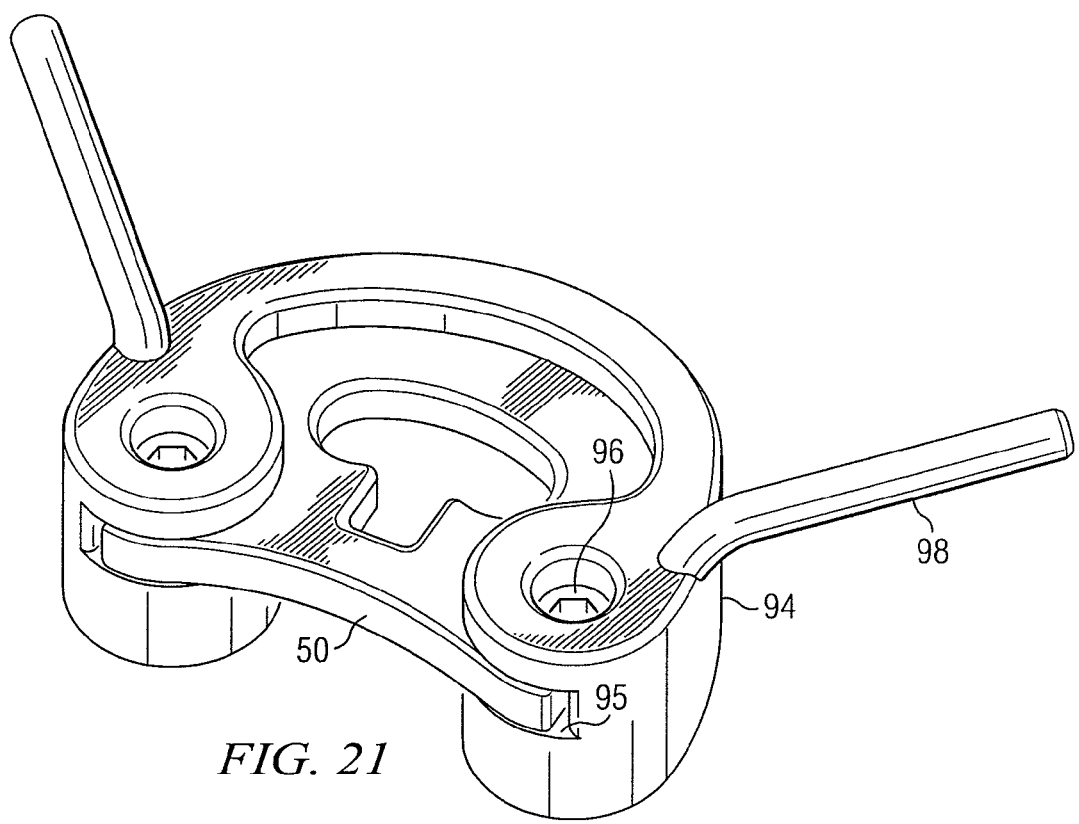
FIGS. 21 through 23 illustrate an example housing, for use with an example adjustment mechanism.
Figure 22:
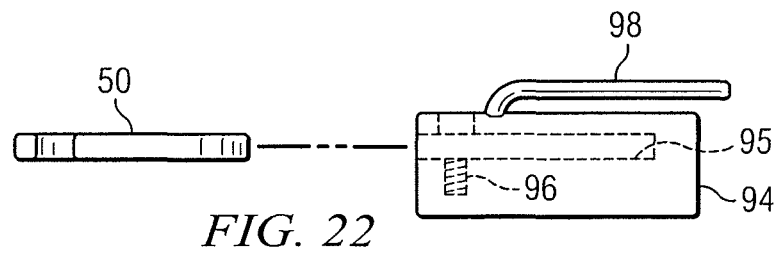
Figure 23:
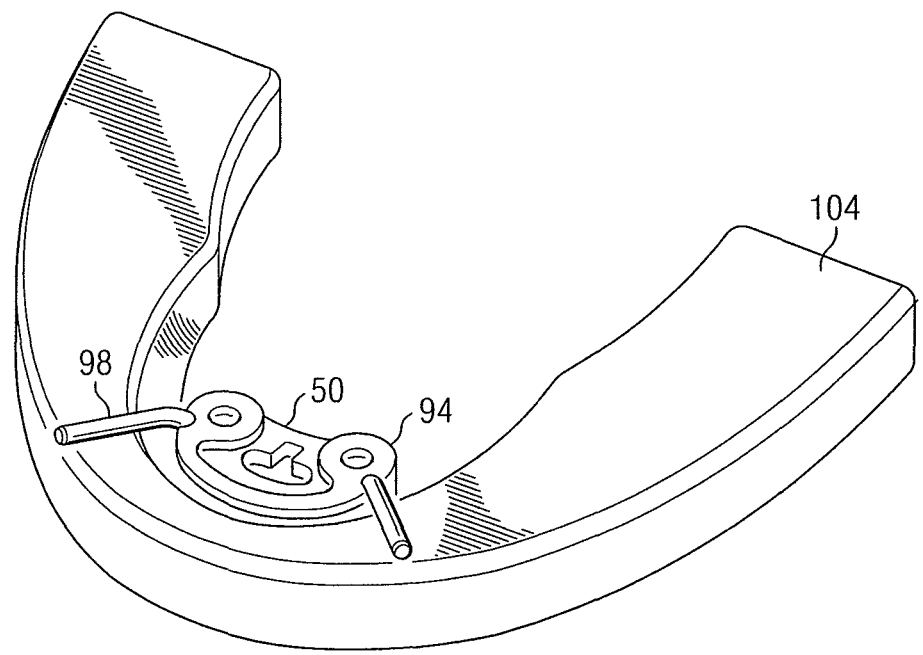

FIGS. 21 through 23 illustrate an example housing 94, for use with an example adjustment mechanism 10. In certain embodiments, adjustment mechanism 10 may include housing 94 to position and secure receiver 50. Housing 94 may be made of any appropriate material, such as metal or hard plastic. In certain embodiments, housing 94 may be integrally formed with lower arch 104. As shown, housing 94 may define recess 95 to accept receiver 50 within housing 94. In certain embodiments, housing 94 may include one or more fasteners 96 to secure receiver 50 within recess 95. In a particular embodiment, fastener 96 may be a threaded setscrew.

In certain embodiments, housing 94 may include one or more projections 98 that may be used to orient and/or secure housing 94 to lower arch 104. In particular embodiments, as in the example shown in FIG. 23, one or more projections 98 may be used to orient housing 94 to lower arch 104. In these embodiments, once housing 94 is properly oriented, housing 94 may be luted to (or otherwise secured to) lower arch 104. In certain embodiments, some or all of projections 98 may be removed before or after housing 94 is completely secured to lower arch 104.

FIGS. 24A through 25C illustrate example receivers 50, for use with an example housing 94. As shown, receiver 50 may have varying dimensions and the location of certain features of receiver 50 may vary. In operation, the use of a particular receiver 50 may be selected to define a prescribed forward location (or range of locations) for lower arch 104 relative to upper arch 102. For example, in the embodiments shown, the use of receiver 50f may allow for lower arch 104 to be positioned further forward with respect to upper arch 102 than with the use of receivers 50d and 50e. In particular embodiments, the use of receivers 50 with varying dimensions may provide an increased range and/or precision for adjusting the forward location of lower arch 104 relative to upper arch 102.

Figure 24A:
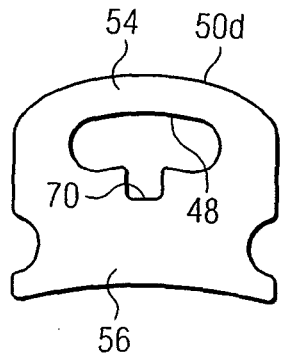
FIGS. 24A through 25C illustrate example receivers, for use with an example housing.
Figure 24B:
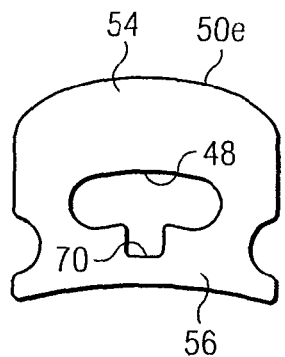
Figure 24C:
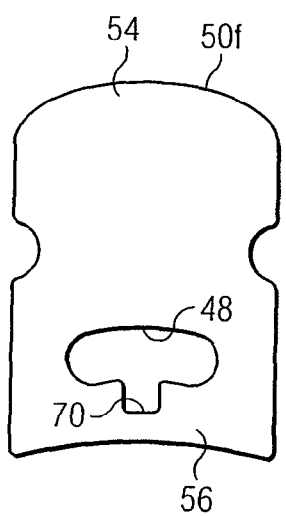
Figure 24D:
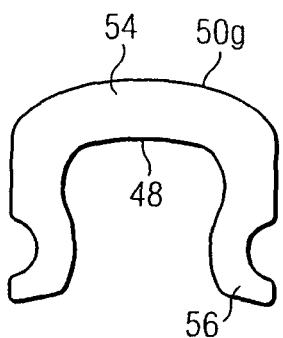

As shown in FIG. 24D, in certain embodiments, receiver 50 may include only a single shelf 54, in which case slot 48 may be fully or partially exposed in the rearward direction. In operation, the use of receiver 50 including only a single shelf 54 (or including notch 70) may allow hook 28 to engage or disengage from shelf 54 of receiver 50 after oral appliance 100 has been inserted into a user's mouth.

Figure 25A:
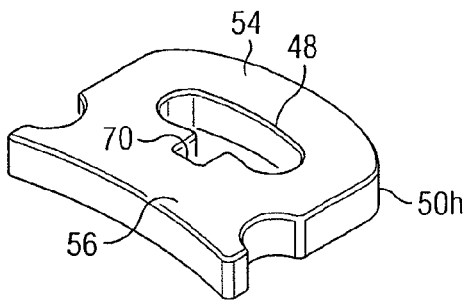
Figure 25B:
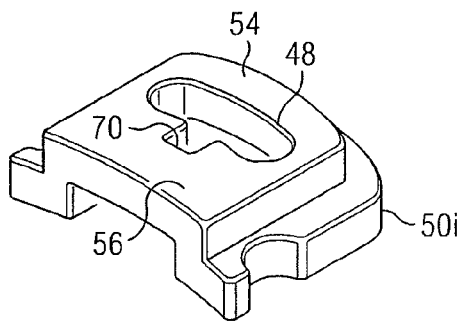
Figure 25C:
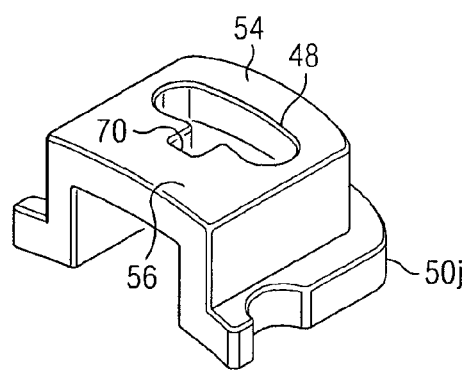

As shown in FIGS. 25A through 25C, receiver may have varying vertical dimensions. In operation, the use of a particular receiver 50 may be selected to define a prescribed vertical separation between upper arch 102 and lower arch 104 and thus a prescribed opening of the user's lower jaw. For example, in the embodiments shown, the use of receiver 50j may allow for greater vertical separation between upper arch 102 and lower arch 104 than the vertical separation allowed with the use of receivers 50h and 50i. In particular embodiments, the use of receivers 50 with varying vertical dimensions may provide an increased range and/or precision for selection of a prescribed opening of the user's lower jaw.

Figure 26:
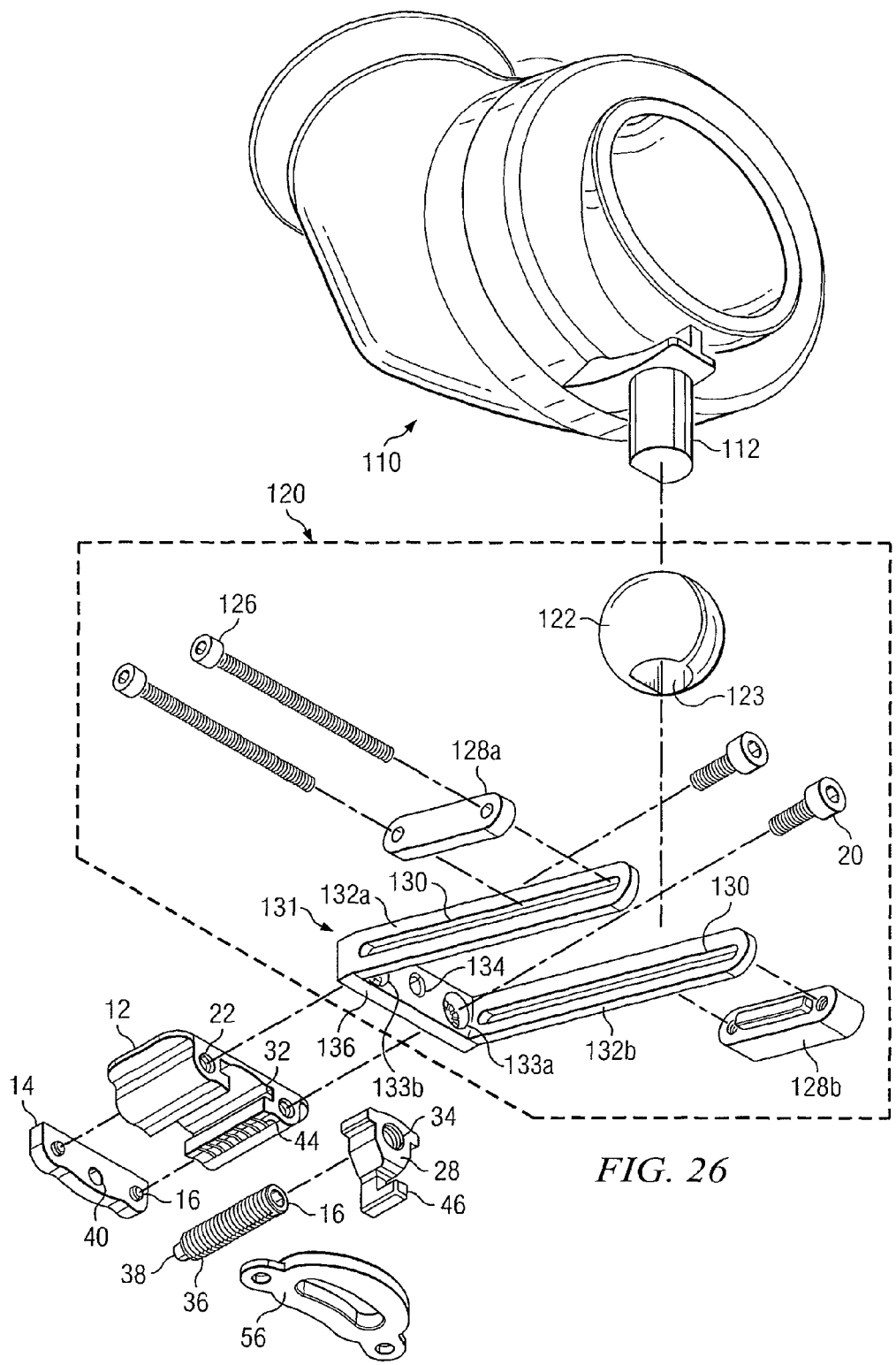
FIG. 26 illustrates an example coupler, an example gas delivery device, and an example body.

FIG. 26 illustrates an example coupler 120, an example gas delivery device 110, and example components of oral appliance 100. In the embodiment shown, coupler 120 includes post 131, clamps 128, fasteners 126, and swivel 122.

Figure 27A:
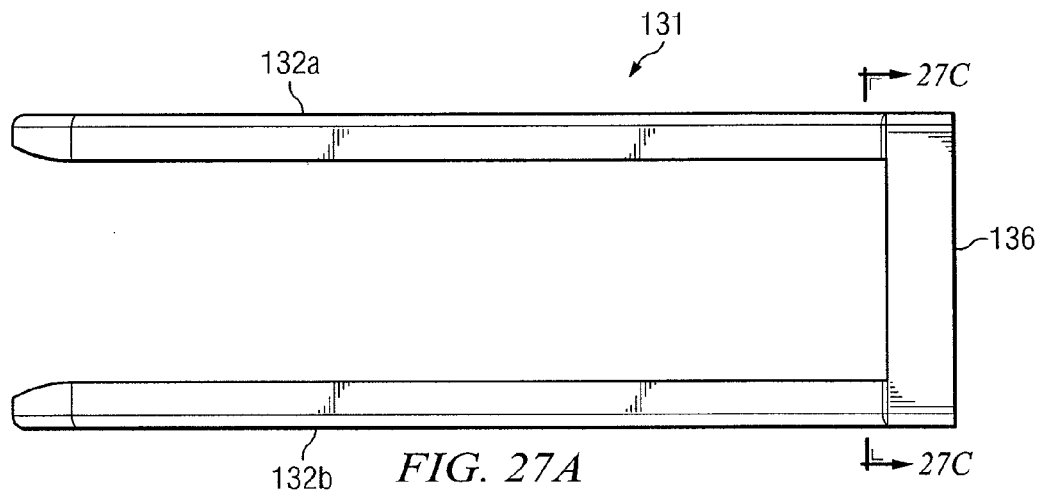
FIGS. 27A-D illustrate various examples of a post.
Figure 27B:
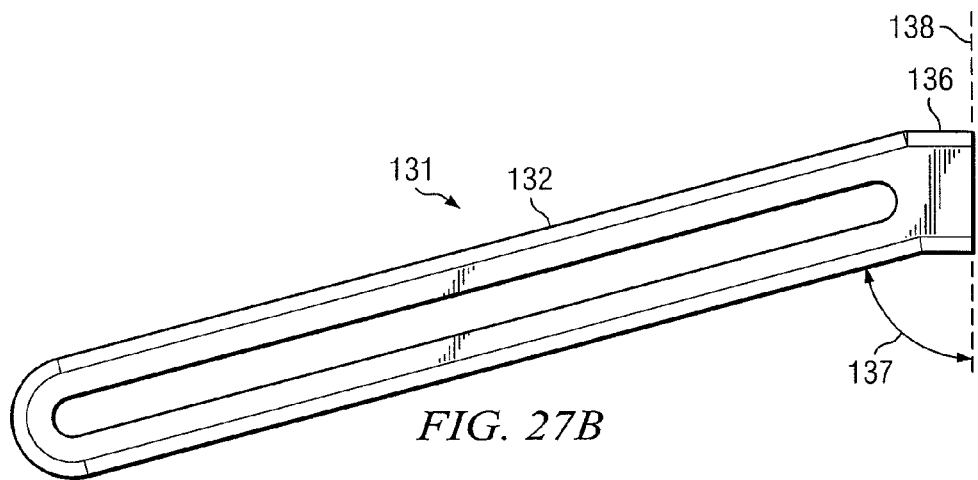

In the depicted embodiment, post 131 includes base 136 and arms 132 configured such that post 131 is substantially U-shaped. Other suitable shapes may be used in various embodiments. For example, post 131 may be substantially V-shaped. FIGS. 27A-D illustrate an example embodiment of post 131. As shown in FIG. 27B, arms 132 in the example embodiment extend at a substantially non-perpendicular angle to base 136. The depicted embodiment in FIG. 27B illustrates that angle 137 (relative to plane 138 extending substantially along the mating surface of base 136) is formed between the junction of base 136 and arms 132. The positioning of arms 132 may provide for a variety of suitable configurations for post 131. In various embodiments, for example, arms 132 may extend at an angle 137 between 60 and 80 degrees. Although any suitable angle 137 may be used, in a particular embodiment, arms 132 may extend substantially perpendicularly from base 136. In the depicted embodiments, arms 132 include channels 130. Channels 130 may be smooth as depicted in FIGS. 26 and 27B. In various embodiments, other suitable shapes may be used. For example, channels 130 may include one or more structures (e.g., notches) to facilitate positioning of clamps 128. Post 131 may be formed of any suitable material, including suitable plastics or metals as examples. In certain embodiments, post 131 may be formed of 304 stainless steel.

FIGS. 28A-29D show several perspectives of one embodiment of clamps 128. In such embodiments, clamps 128 comprise protrusions 129. Protrusions 129 may be used to engage channels 130, as described further below. Protrusions 129 may be configured differently in various embodiments. For example, protrusions 129 may be configured to engage one or more structures in channels 130 to facilitate positioning of clamps 128. Clamps 128 may also include threaded portions that facilitate advancement along channels 130. Clamps 128 may be formed of any suitable material, including suitable plastics or metals as examples. In certain embodiments, clamps 128 may be formed of 304 stainless steel.

In some embodiments, fasteners 126 may be configured in a variety of manners such that fasteners 126 may be suitable for coupling to clamps 128. Fasteners 126 may be threaded and the heads of fasteners 126 may be square, hexagonal, or any other appropriate shape to allow for a rotational force to be applied in order to secure fasteners 126 to clamps 128. In some embodiments, fasteners 126 may not be threaded. The ends of fasteners 126 may have notches or other structures that allow fasteners 126 to lock into place with clamps 128. Fasteners 126 may be formed of any suitable material, including suitable plastics or metals as examples. In certain embodiments, fasteners 126 may be formed of 304 stainless steel.

Figure 30A:
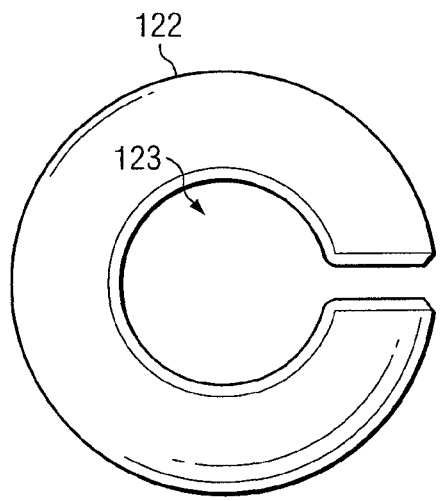
FIGS. 30A-D illustrate examples of a swivel, for use with an example post.
Figure 30B:
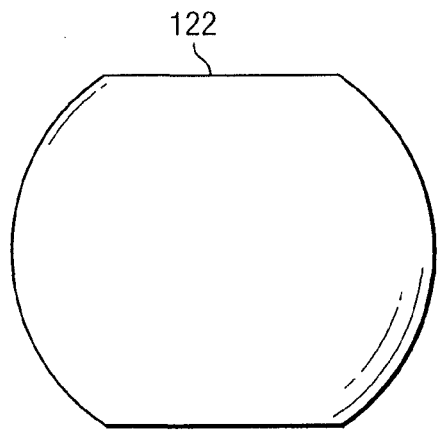
Figure 30C:
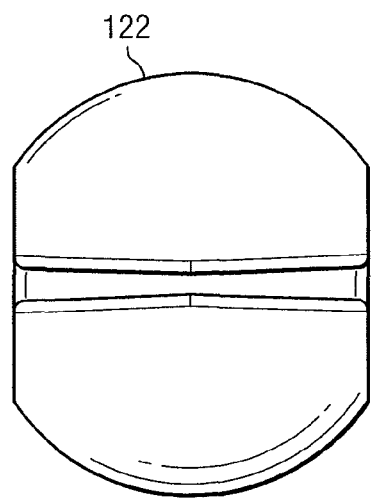
Figure 30D:
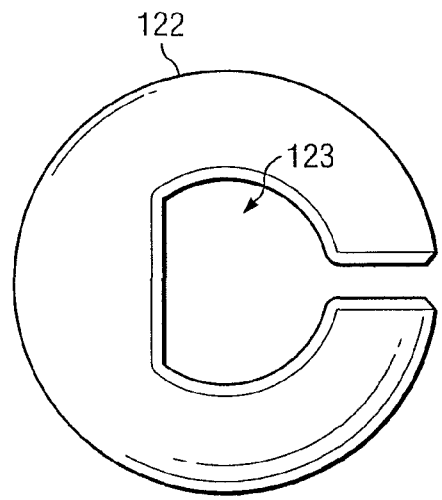

FIGS. 30A-D illustrate various embodiments of swivel 122. In the depicted embodiments, swivel 122 is substantially spherical and includes opening 123. In the example of FIG. 30A, opening 123 is substantially cylindrical while in the example of FIG. 30B, opening 123 includes a D-shaped passageway that may operate to index or orient gas delivery device 110. Additionally, the D-shaped passageway may prevent rotation of swivel 122 relative to a post inserted into opening 123. Other suitable configurations or shapes for opening 123 may be used. FIG. 30B illustrates an embodiment of swivel 122 wherein swivel 122 is substantially spherical with a flat top and bottom portion. Swivel 122 may, in various embodiments, take on other shapes, such as being substantially egg-shaped, and may or may not have a flat top and bottom. Swivel 122 may be formed of any suitable material, including suitable plastics or metals as examples. In particular embodiments, swivel 122 may be formed of acrylonitrile butadiene styrene (ABS) plastic or polycarbonate plastic.

In operation, in various embodiments, coupler 120 may be coupled to body 12 through post 131. In particular embodiments, base 136 may be fastened to body 12 through fastener passages 22 of body 12 and fastener passages 133 of base 136 using fasteners 20. Although two threaded fasteners 20 are illustrated, any suitable technique may be used to couple post 131 to oral appliance 100. For example, post 131 may be integrally formed with one or more components of oral appliance 100. As another example, pins may be used to couple post 131 to oral appliance 100.

Clamps 128 may be used, in some embodiments, to secure swivel 122 to post 131. Clamps 128 may be configured to slideably engage each arm 132 using channels 130 and protrusions 129. Clamps 128 may be secured to arms 132 using fasteners 126 that, for example, pass through clamp 128a, extend across the gap between arms 132a and 132b, and terminate at clamp 128b. In such a manner, the position of swivel 122 relative to base 136 may be determined by the location of clamps 128 along channels 130. Swivel 122 may be positioned between arms 132 and further secured by fasteners 126.

Figure 31A:
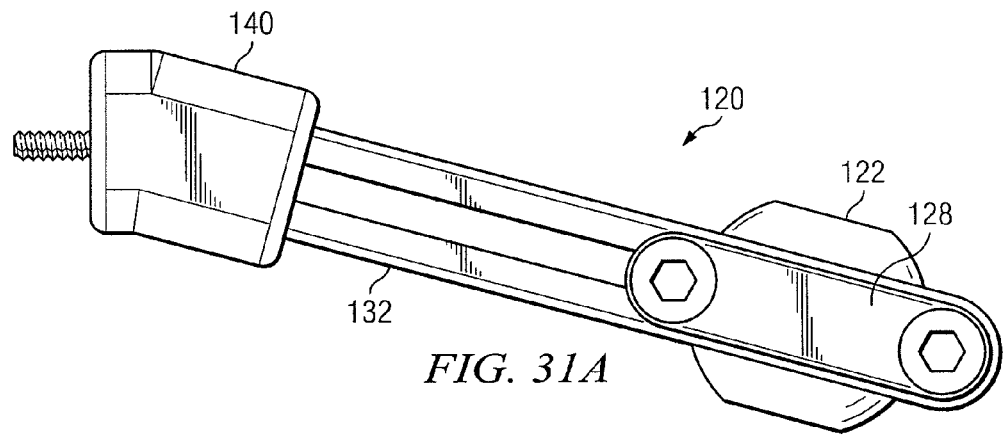
FIGS. 31A-B illustrate examples of a post, for use with an example oral appliance.
Figure 31B:
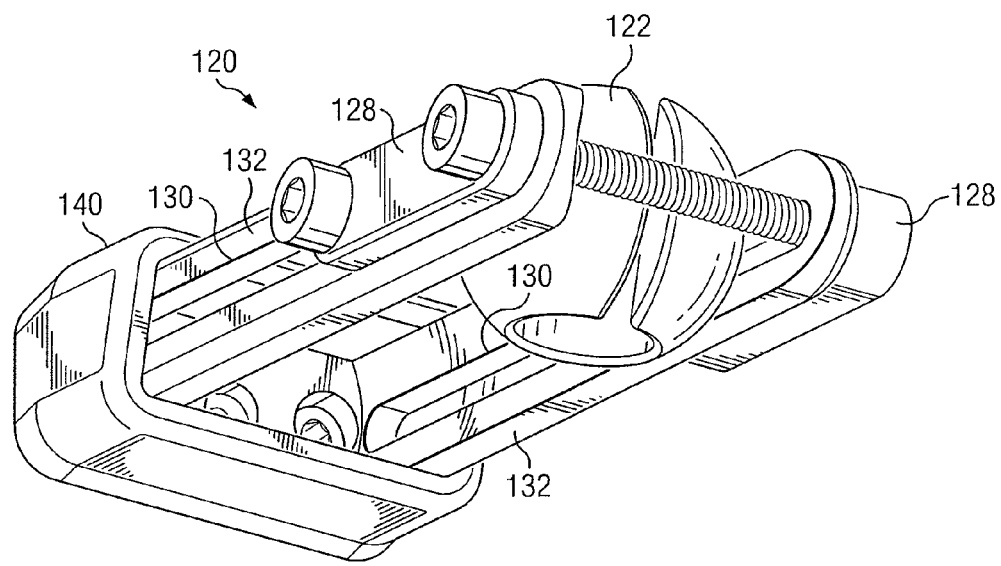

Swivel 122, in various embodiments, may be secured by clamps 128 and fasteners 126 (as depicted in FIGS. 31A-B) in a manner that allows swivel 122 to rotate along at least one axis. Swivel 122 may be configured to engage gas delivery device 110. For example, gas delivery device 110 may include coupling platform 112. In some embodiments, platform 112 and opening 123 may use the same shapes so as to facilitate coupling platform 112 to swivel 122. In particular embodiments, coupling platform 112 may be shaped substantially cylindrically such that it may engage a substantially cylindrical opening 123 of swivel 122. In alternative embodiments, swivel 122 may be integrally formed with gas delivery device 110 or with other components such that no opening is required. In the embodiment shown, swivel 122 includes a notch to allow swivel 122 to be compressed to adjust the diameter of opening 123. Rotating swivel 122 while it is secured to post 131 and platform 112 may allow gas delivery device to be positioned in a suitable manner to properly fit to a patient's face. The freedom of movement allowed by coupler 120 allows gas delivery device 110 to be comfortably and effectively fitted to the patient's unique facial features and preferences. Once they are so fitted, fasteners 126 are tightened so as to maintain this comfortable and effective orientation between gas delivery device 110 and oral appliance 100. In some embodiments, gas delivery device 110 may be further positioned while being secured to platform 112 by moving swivel 122 closer to or away from base 136 of post 131. This, in some embodiments, may be accomplished by sliding clamps 128 along channels 130. During use, oral appliance 100 will be securely in place in the patient's mouth. Because it is connected to gas delivery device 110 through coupler 120, oral appliance 100 acts as an anchor, maintaining the orientation and fit of gas delivery device 110.

Although the described embodiment is with an oral appliance that extends the lower jaw forward to more fully open the breathing passageway of the patient, coupler 120 may also be used with oral appliances that do not perform this function. As discussed above, example oral appliance 100 is used with coupler 120 to anchor gas delivery device 110. In alternative embodiments, other oral appliances may be used to anchor a gas delivery device. For example, an upper arch alone could be used with coupler 120 to connect to gas delivery device 110. Furthermore, oral appliances not shaped as arches could also be used with coupler 120. Indeed, in the context of an oral appliance coupled to a gas delivery device, the term oral appliance is meant to include any device which can fit within the oral cavity and serve as an anchor for the gas delivery device.

The components of coupler 120 may be formed of any suitable material, including suitable plastics or metals as examples. In certain embodiments, post 131 and clamps 128 may be formed of 304 stainless steel. Fasteners 126 may include threaded fasteners, pins, or any other appropriate fastener to couple clamps 128 to arms 132.

Figure 27C:
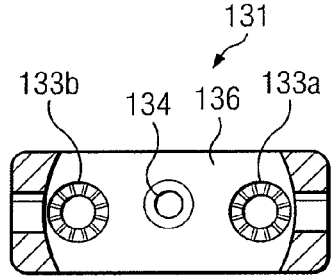
Figure 27D:
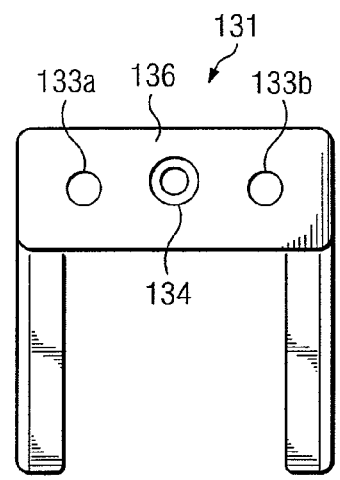
Figure 28A:
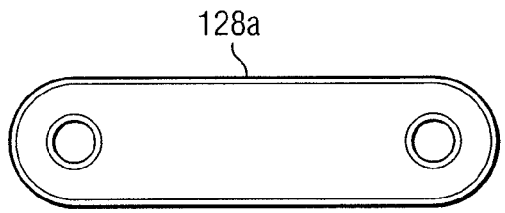
FIGS. 28A-29D illustrate example clamps, for use with an example post.
Figure 28C:
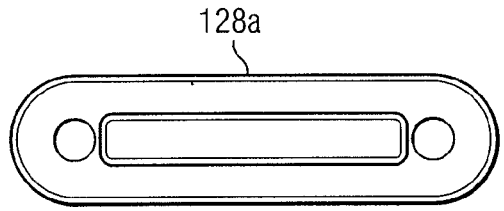
Figure 28B:
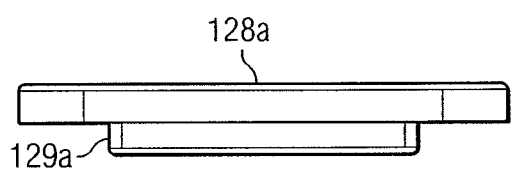
Figure 28D:
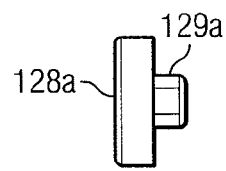
Figure 29A:
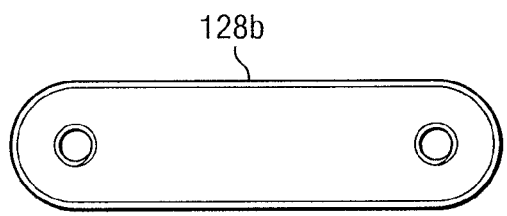
Figure 29C:
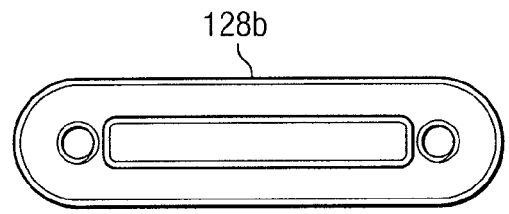
Figure 29B:
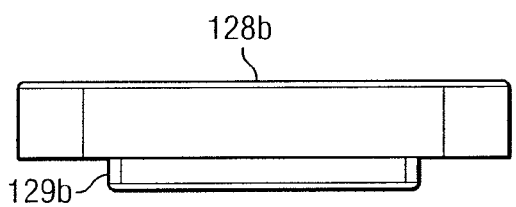
Figure 29D:
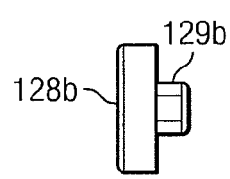

FIG. 27C illustrates passageway 134 which may allow items such as key 80 and post 90 to pass through so that oral appliance 10 may be adjusted while coupled to coupler 120. For example, adjustment key 80 may be inserted through passageway 134 while swivel 122 is engaged or disengaged from post 131 in order to adjust oral appliance 10 (as described above) even though post 131 is secured to body 12.

FIG. 31 illustrate embodiments of coupler 120 including sleeve 140. Sleeve 140, in the depicted embodiments, covers a portion of coupler 120. In various embodiments, sleeve 140 may be made out of rubber, silicon, or other suitable materials. Sleeve 140 may be used to enhance the comfort and/or safety of a user of oral appliance 100 and gas delivery device 110. For example, sleeve 140 may help protect portions of a user's mouth or face from being irritated by the use of coupler 120.

Figure 32:
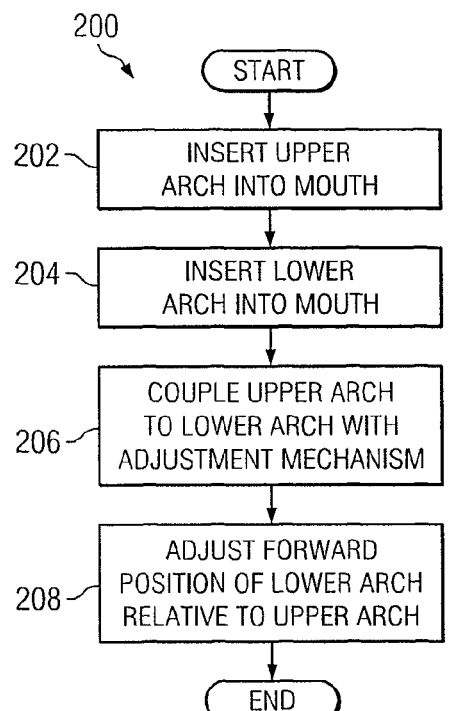
FIG. 32 illustrates an example method of improving a user's breathing.

FIG. 32 illustrates an example method of improving a user's breathing, indicated generally at 200. At step 202, upper arch 102 is inserted into the user's mouth. At step 204, lower arch 104 is inserted into the user's mouth. At step 206, upper arch 102 is coupled to lower arch 104 by adjustment mechanism 10. In certain embodiments, adjustment mechanism 10 includes a body 12 coupled to upper arch 102, an adjustor 36, a hook 28, and a receiver 50 coupled to lower arch 104. In certain embodiments, upper arch 102 is coupled to lower arch 104 by engaging shelf 54 of receiver 50 with arm 46 of hook 28. In particular embodiments, the initial forward position of lower arch 104 relative to upper arch 102 is determined by engaging a particular one of multiple shelves 54 of receiver 50. In alternative embodiments, the initial forward position of lower arch 104 relative to upper arch 102 is determined by engaging shelf 68 of extender 60 coupled to receiver 50. At step 208, the forward position of lower arch 104 relative to upper arch 102 is adjusted to facilitate improved breathing by the user. In certain embodiments, the forward position is adjusted by rotating adjustor 36 using adjustment key 80 or in any other appropriate manner.

Figure 33:
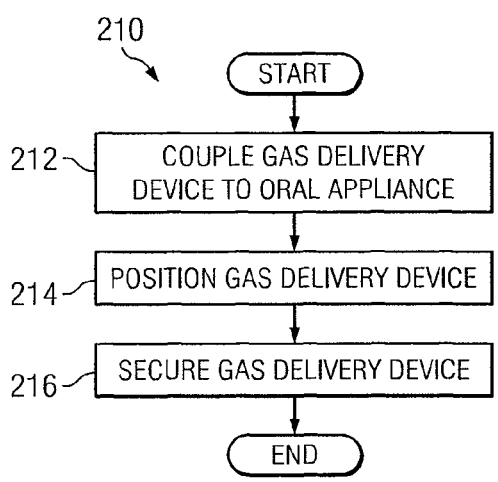
FIG. 33 illustrates an example method of coupling a gas delivery device and an oral appliance.

FIG. 33 illustrates an example method of coupling a gas delivery device to an oral appliance, indicated generally at 210. At step 212, gas delivery device 110 is coupled to oral appliance 100. In certain embodiments, gas delivery device 110 may be coupled to oral appliance 100 using coupler 120 with arms 132, clamps 128, and swivel 122. In particular embodiments, swivel 122 may couple to gas delivery device 110 at mounting platform 112.

At step 214, gas delivery device 110 is positioned. This may be done by adjusting clamps 128 along channels 130. In addition, in some embodiments, swivel 122 may be adjusted in order to further refine the position of gas delivery device 110. In certain embodiments, this may include rotating swivel 122 about at least one axis while swivel 122 is positioned between clamps 128.

At step 216, gas delivery device 110 is secured. This may be accomplished by tightening fasteners 126 so that clamps 128 are secured to arms 132. Tightening fasteners 126 may also secure the position of swivel 122, thus securing the orientation of gas delivery device 110. In some embodiments, this may cause gas delivery device 110 to be positioned appropriately for the user by orienting swivel 122 to post 131. In certain embodiments, post 131 may be coupled to oral appliance 100 at body 12.

Although example methods are described, the steps may be accomplished in any appropriate order. For example, in method 200, inserting the upper and lower arches can be accomplished sequentially, in any order, or simultaneously. As another example, upper arch 102 and lower arch 104 may be coupled subsequent to or prior to inserting upper arch 102 and lower arch 104 into the user's mouth. As another example, the adjustment of the forward position of lower arch 104 relative to upper arch 102 may be performed in measured increments interspersed with trial periods to test the effectiveness of the oral appliance in improving the user's breathing. Method 200 may include checking or verifying the forward position of lower arch 104 relative to upper arch 102 and then repeating step 208 as needed. In certain embodiments, method 200 may include checking or verifying the position of gas delivery device 110 relate to the user and then repeating steps 208 and 210 as needed. The present invention contemplates using methods with additional steps, fewer steps, or different steps, so long as the methods remain appropriate for improving a user's breathing.

Although the present invention has been described in connection with several embodiments, it should be understood that a variety of changes, substitutions, variations, alterations, transformations, and modifications may be suggested to one of skill in the art, and it is intended that the present invention encompass such changes, substitutions, variations, alterations, transformations, and modifications as fall within the spirit and scope of the appended claims.

What is claimed is:

1. An apparatus for coupling an oral appliance to a gas delivery device, comprising:
   a post comprising:
      a base configured to couple to the oral appliance;
      a first arm extending from the base, the first arm defining a channel extending along a portion of the first arm; and
      a second arm extending from the base and extending substantially parallel to the first arm, the second arm defining a channel extending along a portion of the second arm;
   a substantially spherical swivel configured to position the gas delivery device; and
   first and second opposing adjustable clamps;
   wherein the first adjustable clamp comprises a first protrusion shaped to engage and slide along the channel defined by the first arm and the second adjustable clamp comprises a second protrusion shaped to engage and slide along the channel defined by the second arm; and
   wherein the first and second opposing adjustable clamps are together configured to position and secure the location and orientation of the swivel relative to the post by applying a compressive force.

2. The apparatus of claim 1, wherein the post is integrally formed with a component of the oral appliance.

3. The apparatus of claim 1, wherein the swivel defines a substantially cylindrical opening.

4. The apparatus of claim 1, wherein the post comprises stainless steel and the swivel comprises ABS plastic or polycarbonate plastic.

5. The apparatus of claim 1, wherein the swivel is configured to couple to a platform for supporting the gas delivery device.

6. The apparatus of claim 1, wherein the first and second arms extend substantially perpendicularly from the base.

7. The apparatus of claim 1, wherein an angle formed at the junction of the first and second arms and the base is between sixty degrees and eighty degrees relative to a plane extending substantially along the mating surface of the base.

8. The apparatus of claim 1, further comprising a sleeve covering at least a portion of the base.

* * * * *